(12) United States Patent
Jaax et al.

(10) Patent No.: US 8,644,954 B2
(45) Date of Patent: Feb. 4, 2014

(54) METHODS AND SYSTEMS FOR FACILITATING STIMULATION OF ONE OR MORE STIMULATION SITES

(71) Applicant: Boston Scientific Neuromodulation Corporation, Valencia, CA (US)

(72) Inventors: Kristen N. Jaax, Santa Clarita, CA (US); Todd K. Whitehurst, Frederick, MD (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/863,157

(22) Filed: Apr. 15, 2013

(65) Prior Publication Data

US 2013/0231636 A1 Sep. 5, 2013

Related U.S. Application Data

(63) Continuation of application No. 12/188,781, filed on Aug. 8, 2008, now Pat. No. 8,423,155, which is a continuation-in-part of application No. 11/259,176, filed on Oct. 25, 2005, now Pat. No. 7,853,321.

(60) Provisional application No. 60/661,700, filed on Mar. 14, 2005.

(51) Int. Cl.
*A61N 1/00* (2006.01)

(52) U.S. Cl.
USPC ........ 607/116; 607/1; 607/2; 607/45; 607/46; 607/117

(58) Field of Classification Search
USPC .................................... 607/36, 37
See application file for complete search history.

(56) References Cited

U.S. PATENT DOCUMENTS

| | | | |
|---|---|---|---|
| 3,760,984 | A | 9/1973 | Theeuwes |
| 3,845,770 | A | 11/1974 | Theeuwes et al. |
| 3,916,899 | A | 11/1975 | Theeuwes et al. |
| 3,923,426 | A | 12/1975 | Theeuwes |
| 3,987,790 | A | 10/1976 | Eckenhoff et al. |

(Continued)

FOREIGN PATENT DOCUMENTS

| | | |
|---|---|---|
| WO | 0182398 A1 | 11/2001 |
| WO | 03005465 A1 | 1/2003 |

OTHER PUBLICATIONS

"Headache Types," The Complete Guide to Headache, National Headache Foundation, May 9, 2009 http://www.headaches.org/eduicational_modules/completeguide/tension2a.html.

(Continued)

*Primary Examiner* — Nicole F Lavert
(74) *Attorney, Agent, or Firm* — Frommer Lawrence & Haug LLP; Bruce E. Black

(57) ABSTRACT

Methods and systems of facilitating stimulation of a stimulation site within a patient include implanting a distal portion of a stimulating member such that the distal portion of the stimulating member is in communication with a stimulation site located within a patient, securing the distal portion of the stimulating member at a first securing site with a first securing device, forming at least two curves of opposite concavity with a proximal portion of the stimulating member, securing the stimulating member at a second securing site with a second securing device, and coupling a proximal end of the stimulating member to a stimulator. In some examples, the at least two curves of opposite concavity are located in between the first and second securing devices.

20 Claims, 18 Drawing Sheets

(56) References Cited

U.S. PATENT DOCUMENTS

| | | |
|---|---|---|
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,487,603 A | 12/1984 | Harris |
| 4,562,751 A | 1/1986 | Nason et al. |
| 4,627,850 A | 12/1986 | Deters et al. |
| 4,678,408 A | 7/1987 | Nason et al. |
| 4,685,903 A | 8/1987 | Cable et al. |
| 4,692,147 A | 9/1987 | Duggan |
| 4,725,852 A | 2/1988 | Gamblin et al. |
| 4,865,845 A | 9/1989 | Eckenhoff et al. |
| 4,867,164 A | 9/1989 | Zabara |
| 5,057,318 A | 10/1991 | Magruder et al. |
| 5,059,423 A | 10/1991 | Magruder et al. |
| 5,080,653 A | 1/1992 | Voss et al. |
| 5,097,122 A | 3/1992 | Colman et al. |
| 5,112,614 A | 5/1992 | Magruder et al. |
| 5,137,727 A | 8/1992 | Eckenhoff |
| 5,193,539 A | 3/1993 | Schulman et al. |
| 5,193,540 A | 3/1993 | Schulman et al. |
| 5,215,086 A | 6/1993 | Terry, Jr. et al. |
| 5,218,959 A | 6/1993 | Fenster |
| 5,234,692 A | 8/1993 | Magruder et al. |
| 5,234,693 A | 8/1993 | Magruder et al. |
| 5,273,053 A | 12/1993 | Pohndorf |
| 5,312,439 A | 5/1994 | Loeb |
| 5,376,108 A | 12/1994 | Collins et al. |
| 5,400,784 A | 3/1995 | Durand et al. |
| 5,501,703 A | 3/1996 | Holsheimer et al. |
| 5,540,734 A | 7/1996 | Zabara |
| 5,584,874 A | 12/1996 | Rugland et al. |
| 5,603,730 A | 2/1997 | Romkee |
| 5,728,396 A | 3/1998 | Peery et al. |
| 5,938,688 A | 8/1999 | Schiff |
| 6,016,449 A | 1/2000 | Fischell et al. |
| 6,051,017 A | 4/2000 | Loeb et al. |
| 6,122,545 A | 9/2000 | Struble et al. |
| 6,161,044 A | 12/2000 | Silverstone |
| 6,164,284 A | 12/2000 | Schulman et al. |
| 6,185,452 B1 | 2/2001 | Schulman et al. |
| 6,208,894 B1 | 3/2001 | Schulman et al. |
| 6,219,580 B1 | 4/2001 | Faltys et al. |
| 6,272,382 B1 | 8/2001 | Faltys et al. |
| 6,280,873 B1 | 8/2001 | Tsukamoto |
| 6,308,101 B1 | 10/2001 | Faltys et al. |
| 6,368,315 B1 | 4/2002 | Gillis et al. |
| 6,381,496 B1 | 4/2002 | Meadows et al. |
| 6,393,325 B1 | 5/2002 | Mann et al. |
| 6,458,171 B1 | 10/2002 | Tsukamoto |
| 6,487,446 B1 | 11/2002 | Hill et al. |
| 6,505,075 B1 | 1/2003 | Weiner |
| 6,516,227 B1 | 2/2003 | Meadows et al. |
| 6,539,263 B1 | 3/2003 | Schiff et al. |
| 6,553,263 B1 | 4/2003 | Meadows et al. |
| 6,596,439 B1 | 7/2003 | Tsukamoto et al. |
| 6,605,382 B2 | 8/2003 | Ruth et al. |
| 6,605,383 B1 | 8/2003 | Wu |
| 6,607,843 B2 | 8/2003 | Ruth, II et al. |
| 6,620,151 B2 | 9/2003 | Blischak et al. |
| 6,666,845 B2 | 12/2003 | Hooper et al. |
| 6,735,475 B1 | 5/2004 | Whitehurst et al. |
| 6,740,072 B2 | 5/2004 | Starkweather et al. |
| 6,760,626 B1 | 7/2004 | Boveja |
| 6,770,067 B2 | 8/2004 | Lorenzen et al. |
| 6,782,292 B2 | 8/2004 | Whitehurst |
| 7,082,337 B2 | 7/2006 | Sommer et al. |
| 7,187,981 B2 | 3/2007 | Tanaka |
| 7,389,149 B2 | 6/2008 | Rossing et al. |
| 7,774,072 B2 | 8/2010 | Gerber |
| 7,848,803 B1 | 12/2010 | Jaax et al. |
| 7,853,321 B2 | 12/2010 | Jaax et al. |
| 8,224,451 B2 | 7/2012 | Jaax et al. |
| 8,315,704 B2 | 11/2012 | Jaax et al. |
| 2001/0046625 A1 | 11/2001 | Ruth et al. |
| 2001/0053476 A1 | 12/2001 | Ruth et al. |
| 2002/0013612 A1 | 1/2002 | Whitehurst |
| 2005/0004637 A1 | 1/2005 | Singhal et al. |
| 2006/0206165 A1 | 9/2006 | Jaax et al. |
| 2008/0132980 A1 | 6/2008 | Gerber |
| 2011/0060382 A1 | 3/2011 | Jaax et al. |
| 2011/0066197 A1 | 3/2011 | Jaax et al. |

OTHER PUBLICATIONS

"Medtronic begins study of occipital nerve stimulation for chronic, refactory migraine headaches. (Medtronic Inc.) (Brief Article)." Transplant News, Transplant Communications, Inc. 2004, HighBeam Research, May 9, 2009.

"Physician's Manual," Sep. 2001, Cyberonics, Inc., Houston, TX.

Davis, R., "Notes Regarding Discussion with Dr. Giancarlo Barolat," Aug. 11, 2005.

Shellock, F. G. et al., "Vagus Nerve Stimulation Therapy System: In Vitro Evaluation of Magnetic Resonance Imaging-Related Heating and Function at 1.5 and 3 Tesla," Cyperonics, Houston, TX, 2006.

Official Communication for U.S. Appl. No. 11/256,356 mailed May 15, 2009.

Official Communication for U.S. Appl. No. 11/259,176 mailed Jan. 30, 2008.

Official Communication for U.S. Appl. No. 11/259,176 mailed Jun. 26, 2008.

Official Communication for U.S. Appl. No. 11/259,176 mailed Nov. 18, 2008.

Official Communication for U.S. Appl. No. 11/259,176 mailed Apr. 29, 2009.

Official Communication for U.S. Appl. No. 11/259,176 mailed Oct. 19, 2009.

Official Communication for U.S. Appl. No. 11/259,176 mailed Mar. 29, 2010.

Official Communication for U.S. Appl. No. 11/259,176 mailed Oct. 13, 2010.

Official Communication for U.S. Appl. No. 11/728,816 mailed Jan. 22, 2010.

Official Communication for U.S. Appl. No. 11/728,816 mailed Jul. 30, 2010.

Official Communication for U.S. Appl. No. 11/728,816 mailed Sep. 29, 2010.

Official Communication for U.S. Appl. No. 12/188,781 mailed Feb. 4, 2010.

Official Communication for U.S. Appl. No. 12/188,781 mailed Jul. 29, 2010.

Official Communication for U.S. Appl. No. 12/188,781 mailed Nov. 5, 2010.

Official Communication for U.S. Appl. No. 12/188,781 mailed Apr. 8, 2011.

Official Communication for U.S. Appl. No. 12/188,781 mailed Jun. 10, 2011.

Official Communication for U.S. Appl. No. 12/188,781 mailed Nov. 22, 2011.

Official Communication for U.S. Appl. No. 12/188,781 mailed Feb. 10, 2012.

Official Communication for U.S. Appl. No. 12/186,781 mailed Jun. 1, 2012.

Official Communication for U.S. Appl. No. 12/188,781 mailed Oct. 16, 2012.

Official Communication for U.S. Appl. No. 12/188,781 mailed Nov. 2, 2012.

Official Communication for U.S. Appl. No. 12/188,781 mailed Feb. 8, 2013.

Official Communication for U.S. Appl. No. 12/940,862 mailed Dec. 28, 2011.

(56) References Cited

OTHER PUBLICATIONS

Official Communication for U.S. Appl. No. 12/940,862 mailed Apr. 19, 2012.

Official Communication for U.S. Appl. No. 12/940,862 mailed Aug. 23, 2012.

Official Communication for U.S. Appl. No. 12/948,416 mailed Dec. 13, 2011.

Official Communication for U.S. Appl. No. 12/948,416 mailed Mar. 27, 2012.

METHODS AND SYSTEMS FOR FACILITATING STIMULATION OF ONE OR MORE STIMULATION SITES

RELATED APPLICATIONS

This application is a continuation of U.S. patent application Ser. No. 12/188,781, filed Aug. 8, 2008, now U.S. Pat. No. 8,423,155, which is a continuation-in-part of U.S. application Ser. No. 11/259,176, filed Oct. 25, 2005, now U.S. Pat. No. 7,853,321, which application claims the benefit of U.S. Provisional Application Ser. No. 60/661,700 filed Mar. 14, 2005. All applications are incorporated herein by reference in their respective entireties.

BACKGROUND

The public health significance of many medical, psychiatric, and neurological conditions and/or disorders is often overlooked, probably because of their episodic nature and the lack of mortality attributed to them. However, some medical conditions, such as headaches and facial pain, are often incapacitating, with considerable impact on social activities and work, and may lead to the significant consumption of drugs.

Migraine headaches are a particular form of headache, usually very intense and disabling. Migraines are a neurological disease thought to be of vascular origin. They are characterized by attacks of sharp pain usually involving one half of the skull and may be accompanied by nausea, vomiting, phonophobia, photophobia and occasionally visual, olfactory or balance disturbances known as aura. The symptoms and their timing vary considerably among migraine sufferers and, to a lesser extent, from one migraine attack to the next. Migraine is often connected with the expansion of the blood vessels of the head and neck.

Conventional treatments for migraines focus on three areas: trigger avoidance, symptomatic control, and preventive drugs. Each of these will be discussed below.

In a minority of patients, the incidence of migraines can be reduced through diet changes to avoid certain chemicals that serve as triggers for migraines. These chemical triggers may be present in such foods as cheddar cheese and chocolate, and in most alcoholic beverages. Other triggers may be situational and some can be avoided through lifestyle changes. Such triggers may include particular points in the menstrual cycle, certain weather patterns, or hunger. Bright flashing lights may also be a trigger. Most migraine sufferers are sensitive to and avoid bright or flickering lights.

If a migraine occurs despite trigger avoidance, the next step in treatment is symptomatic control. Caffeine and simple pain killers, analgesics, such as paracetamol, aspirin or low doses of codeine are sometimes, but not often, effective. Narcotic pain medications, such as heroin, morphine, and other opiates, provide variable relief. However, many of these drugs are addictive and can cause undesirable side effects.

Various drugs may also be administered on a regular basis to prevent the onset of migraines. Exemplary preventive drugs include beta blockers (e.g., propranolol or atenolol), antidepressants, and antispasmodic drugs. However, many of these drugs are ineffective in preventing migraines.

SUMMARY

Methods of facilitating stimulation of a stimulation site within a patient include implanting a distal portion of a stimulating member such that the distal portion of the stimulating member is in communication with a stimulation site located within the patient, securing the distal portion of the stimulating member at a first securing site with a first securing device, forming at least two curves of opposite concavity with a proximal portion of the stimulating member, securing the stimulating member at a second securing site with a second securing device, and coupling a proximal end of the stimulating member to a stimulator. In some examples, the at least two curves of opposite concavity are located in between the first and second securing devices.

Systems for facilitating stimulation of a stimulation site within a patient include a stimulating member having a distal portion configured to be in communication with a stimulation site located within the patient and a proximal portion configured to be formed into at least two curves of opposite concavity, a stimulator coupled to a proximal end of the stimulating member, a first securing device configured to secure the stimulating member to a first securing site to maintain the distal portion of the stimulating member in communication with the stimulation site, and a second securing device configured to secure the stimulating member at a second securing site. In some examples, the proximal portion configured to be formed into the at least two curves of opposite concavity is configured to be located in between the first and second securing devices.

BRIEF DESCRIPTION OF THE DRAWINGS

The accompanying drawings illustrate various embodiments of the principles described herein and are a part of the specification. The Illustrated embodiments are merely examples and do not limit the scope of the disclosure.

Throughout the drawings, identical reference numbers designate similar, but not necessarily identical, elements.

DETAILED DESCRIPTION

Methods and systems for facilitating stimulation of at least one stimulation site within a patient are described herein. The methods and systems may be used to treat a variety of medical conditions such as, but not limited to, headaches, occipital neuralgia, facial pain, and/or conditions treated with spinal cord stimulation.

In some examples, a distal portion of a stimulating member (e.g., a lead and/or a catheter) is implanted such that it is in communication with a stimulation site located within a patient. A first securing device may be used to secure the distal portion of the stimulating member at a first securing site. At least two curves of opposite concavity are formed with a proximal portion of the stimulating member. A second securing device may be used to secure the stimulating member at a second securing site. The location of the second securing site is selected such that the at least two curves of opposite concavity are positioned in between the first and second securing devices. A proximal end of the stimulating member may be coupled to a stimulator, which may be configured to apply a stimulus to the stimulation site via the stimulating member.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase In one embodiment" in various places in the specification are not necessarily all referring to the same embodiment.

Figure 1A:
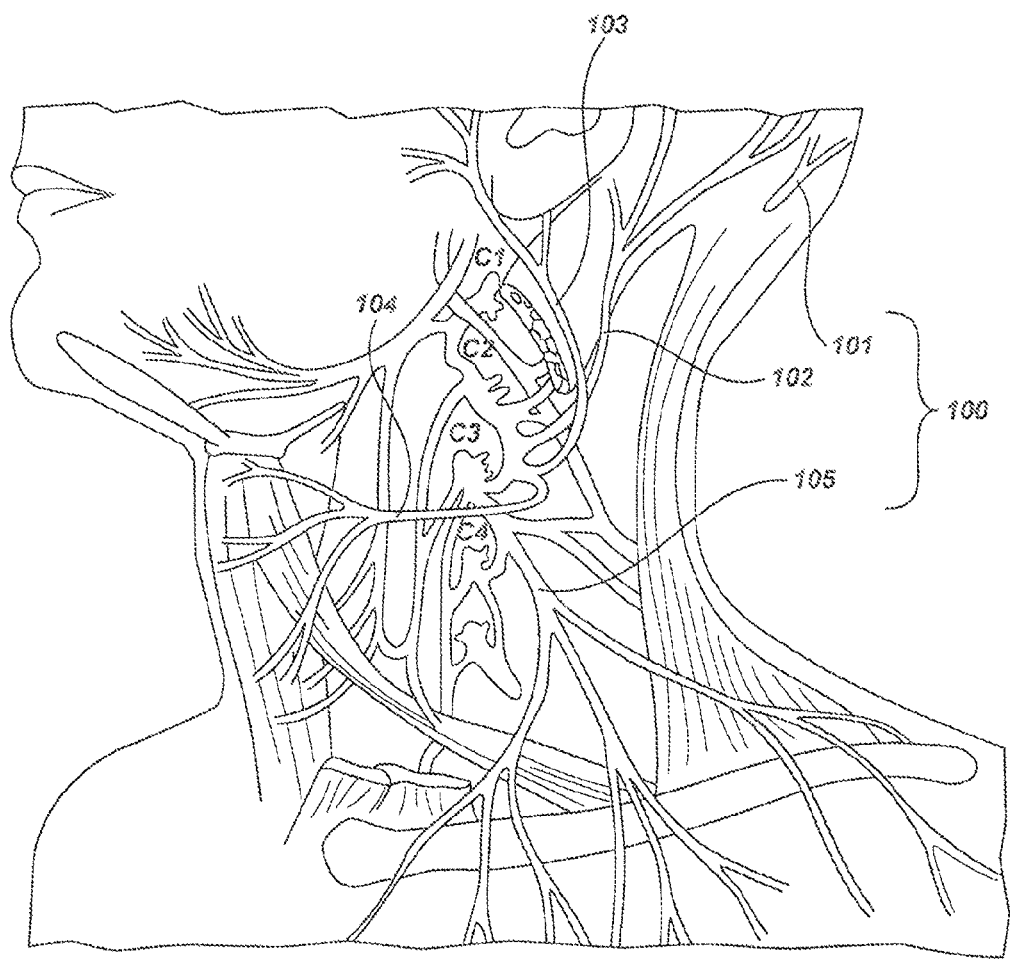
FIG. 1A depicts the upper cervical spine area of a patient and shows a number of nerves originating in the upper cervical spine area.

FIG. 1A depicts the upper cervical spine (C1-C4) area of a patient. As shown in FIG. 1A, a number of nerves arise from the upper cervical spine (C1-C4). Examples of such nerves include, but are not limited to, the greater occipital nerve(s) 101, lesser occipital nerve(s) 102, greater auricular nerve(s) 103, transverse cervical nerve(s) 104, supraclavicular nerve(s) 105, and/or branches of any of these nerves.

Figure 1B:
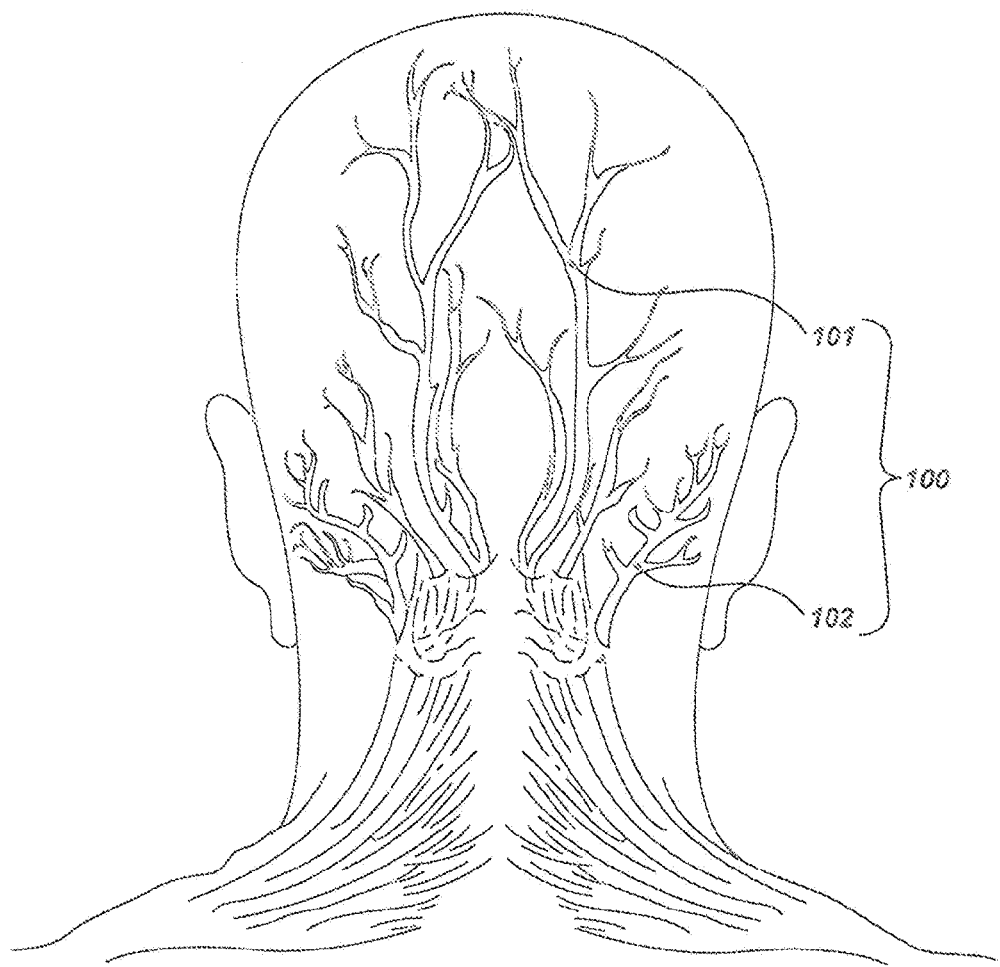
FIG. 1B depicts the occipital nerves in the back of the head and upper neck area of a patient.

FIG. 1B depicts the occipital nerves 100 in the back of the head and upper neck area of a patient. As shown in FIG. 1B, the occipital nerves 100 are divided into greater 101 and lesser 102 occipital nerves. The occipital nerves 100 lie subcutaneously in the back of the head and upper neck and are therefore are relatively easily accessed.

Figure 1C:
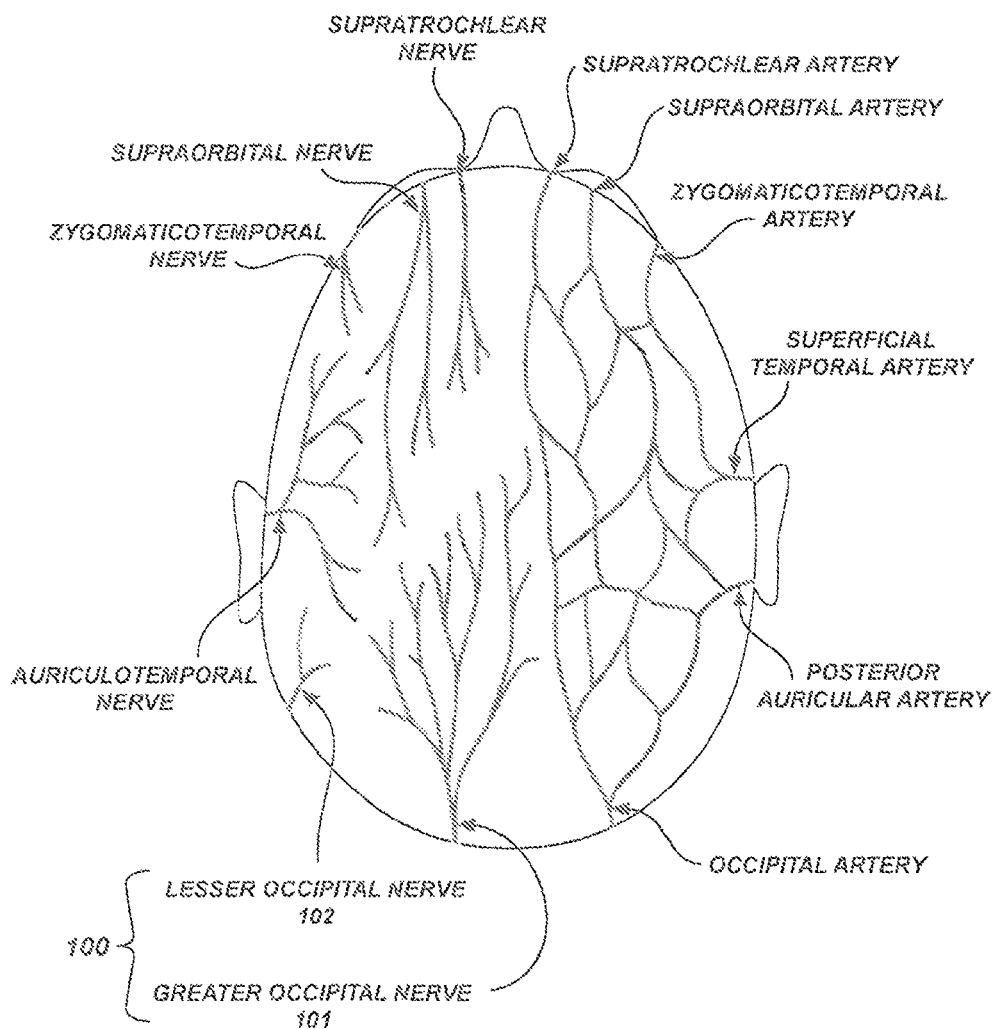
FIG. 1C illustrates a view of the major nerves and arteries in the human head as viewed from above looking down on the top or superior part of the head.

FIG. 1C illustrates a view of the major nerves and arteries in the human head as viewed from above looking down on the top or superior part of the head. As shown in FIG. 1C, the greater occipital nerves 101 extend to and across some of the top or superior portion of the head. The lesser occipital nerves 102 may also extend to or near the top or superior portion of the head.

It is believed that applying a stimulus to one or more of the nerves within in the head and/or neck may be effective in treating one or more medical conditions. For example, the stimulus may be configured to alleviate or eliminate headache (e.g., migraine). However, it will be recognized that any other medical condition (e.g., occipital neuralgia, facial pain, conditions treated with spinal cord stimulation, erectile dysfunction, overactive bladder, etc.) may be treated in accordance with the systems and methods described herein.

Consequently, a stimulator may be implanted within a patient to deliver a stimulus to one or more stimulation sites within the head and/or neck in order to treat one or more medical conditions. The present specification describes methods and systems for implanting such a stimulator within the patient.

The stimulation sites referred to herein may include any nerve, tissue, blood vessel, or other area within a patient. It will be recognized that although the exemplary stimulation sites described in connection with the examples given herein are located within the head and/or neck, one or more of the stimulation sites may additionally or alternatively be located anywhere within a patient. For example, the methods and systems described herein may be used in connection with spinal cord stimulation, wherein the stimulation site is located along the spinal cord and wherein the stimulator is implanted at a surgically convenient location (e.g., within the buttocks).

As used herein, and in the appended claims, the term "stimulator" is used broadly to refer to any device that delivers a stimulus, such as an electrical stimulation current, one or more drugs, chemical stimulation, thermal stimulation, electromagnetic stimulation, mechanical stimulation, blocking stimulation, and/or any other suitable stimulation to a stimulation site. Thus, the term "stimulator" includes, but is not limited to, a microstimulator, an implantable pulse generator (IPG), a system control unit, an external trial stimulator, or similar device.

Figure 2:
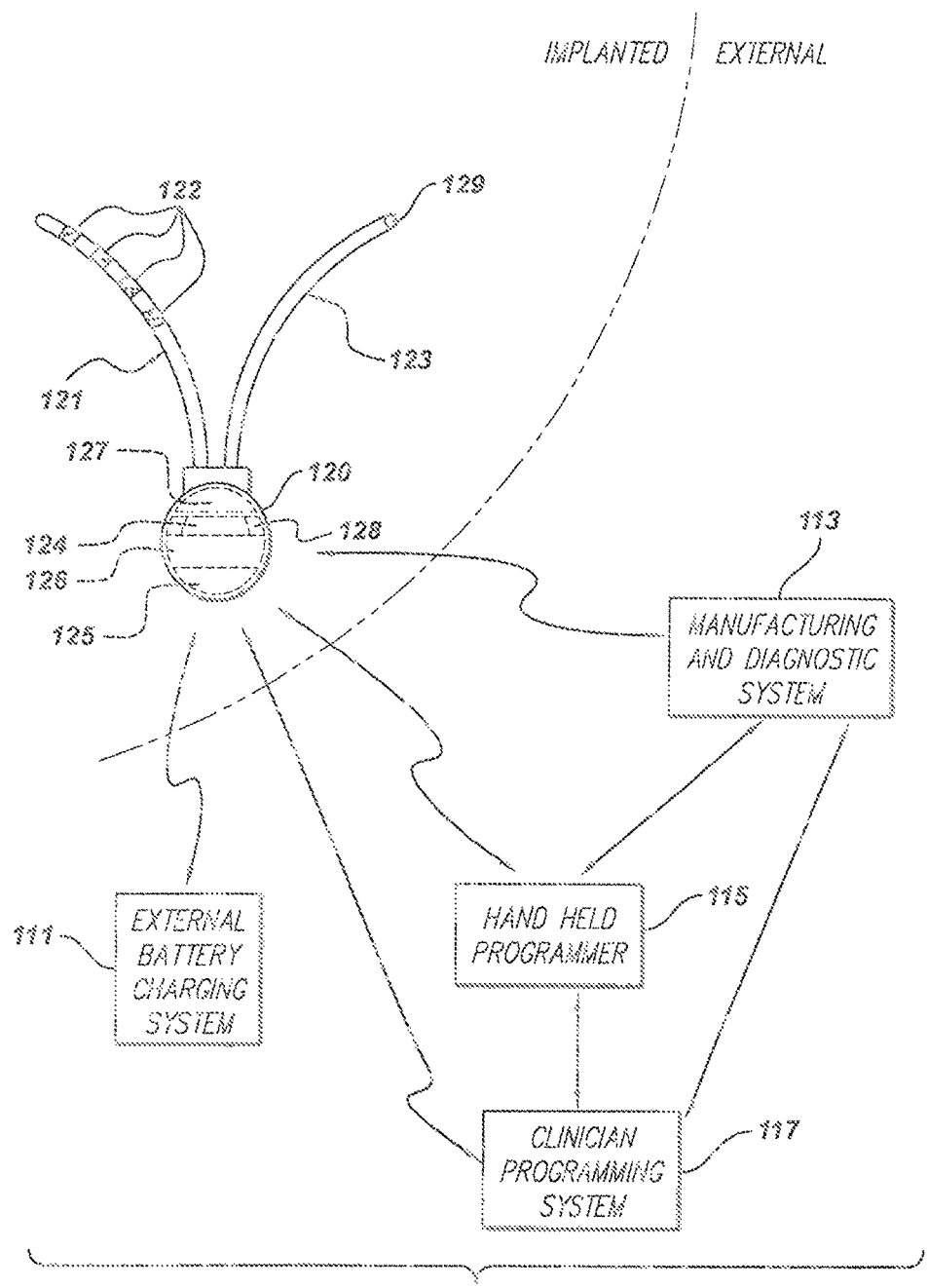
FIG. 2 illustrates an exemplary implantable stimulator according to principles described herein.

To facilitate an understanding of the methods and systems described herein, a more detailed description of a stimulator and its operation will now be given with reference to the figures. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied to a stimulation site. It will be recognized that the at least one lead 121 may include any number of electrodes 122 arranged in any configuration as best serves a particular application.

As illustrated in FIG. 2, the stimulator 120 includes a number of components. It will be recognized that the stimulator 120 may include additional and/or alternative components as may serve a particular application. A power source 125 is configured to output voltage used to supply the various components within the stimulator 120 with power and/or to generate the power used for electrical stimulation. The power source 125 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 125 may be recharged using an external charging system. One type of rechargeable power supply that may be used is described in U.S. Pat. No. 6,596,439, which is incorporated herein by reference in its entirety. Other battery construction techniques that may be used to make the power source 125 include those shown, e.g., in U.S. Pat. Nos. 6,280,873; 6,458,171; 6,605,383; and 6,607,843, all of which are incorporated herein by reference in their respective entireties.

The stimulator 120 may also include a coil 128 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 125.

For example, an external battery charging system (EBCS) 111 may be provided to generate power that is used to recharge the power source 125 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120. Furthermore, it will be recognized that the functions performed by any two or more of the external devices shown in FIG. 2 may be performed by a single external device.

The stimulator 120 may also include electrical circuitry 124 configured to generate the electrical stimulation current that is delivered to a stimulation site via one or more of the electrodes 122. For example, the electrical circuitry 124 may include one or more processors, capacitors, integrated circuits, resistors, coils, and/or any other component configured to generate electrical stimulation current.

Additionally, the exemplary stimulator 120 shown in FIG. 2 may be configured to provide drug stimulation to a patient by applying one or more drugs at a stimulation site within the patient. To this end, a pump 127 may also be included within the stimulator 120. The pump 127 is configured to store and dispense one or more drugs, for example, through a catheter 123. The catheter 123 is coupled at a proximal end to the stimulator 120 and may have an infusion outlet 129 for infusing dosages of the one or more drugs at the stimulation site. In some embodiments, the stimulator 120 may include multiple catheters 123 and/or pumps 127 for storing and infusing dosages of the one or more drugs at the stimulation site.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 allows a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site. For example, at least one of the pulse width, frequency, amplitude, and inter-pulse interval (i.e., the delay between adjacent stimulation pulses) may be continuously adjusted to minimize patient accommodation to the stimulation.

The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

The stimulator 120 of FIG. 2 is illustrative of many types of stimulators that may be used in accordance with the systems and methods described herein. For example, the stimulator 120 may include an implantable pulse generator (IPG), a spinal cord stimulator (SCS), a deep brain stimulator, a drug pump, an external trial stimulator, or any other type of stimulation device configured to deliver a stimulus to a stimulation site within a patient. Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

The stimulator 120 of FIG. 2 may alternatively include a microstimulator. Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
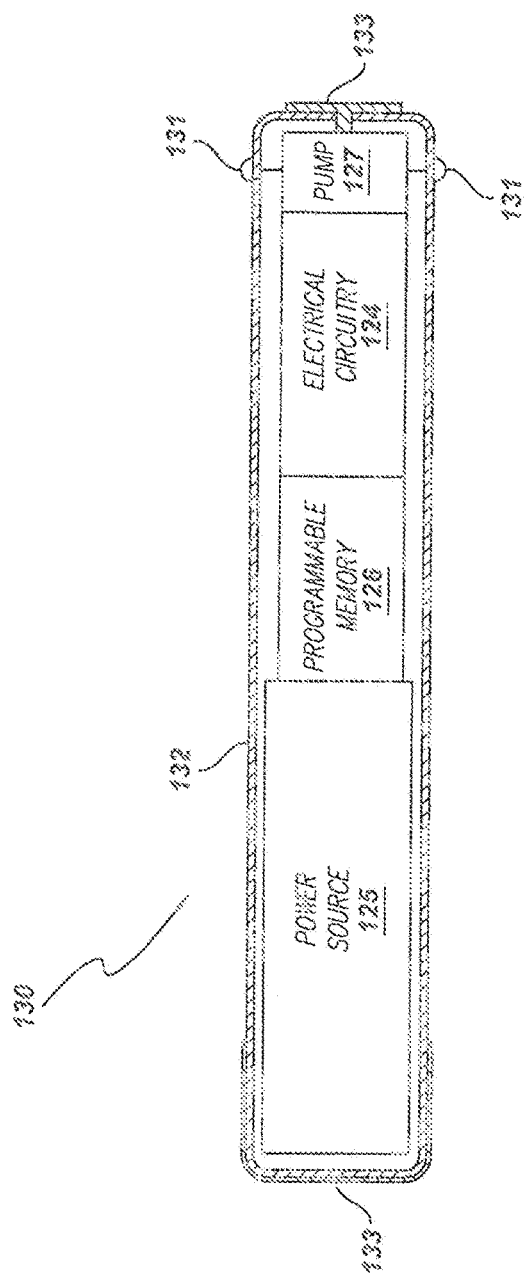
FIG. 3 illustrates an exemplary microstimulator according to principles described herein.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 125, the programmable memory 126, the electrical circuitry 124, and the pump 127 described in connection with FIG. 2. These components are housed within a capsule 132. The capsule 132 may be a thin, elongated cylinder or any other shape as best serves a particular application. The shape of the capsule 132 may be determined by the structure of the desired stimulation site and the method of implantation. In some examples, the microstimulator 130 may include two or more leadless electrodes 133 disposed on the outer surface of the microstimulator 130.

The external surfaces of the microstimulator 130 may advantageously be composed of biocompatible materials. For example, the capsule 132 may be made of glass, ceramic, metal, or any other material that provides a hermetic package that will exclude water vapor but permit passage of electromagnetic fields used to transmit data and/or power. The electrodes 133 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 131 configured to dispense one or more drugs directly at a stimulation site. Alternatively, one or more catheters may be coupled to the infusion outlets 131 to deliver the drug therapy to a treatment site some distance from the body of the microstimulator 130.

Figure 4:
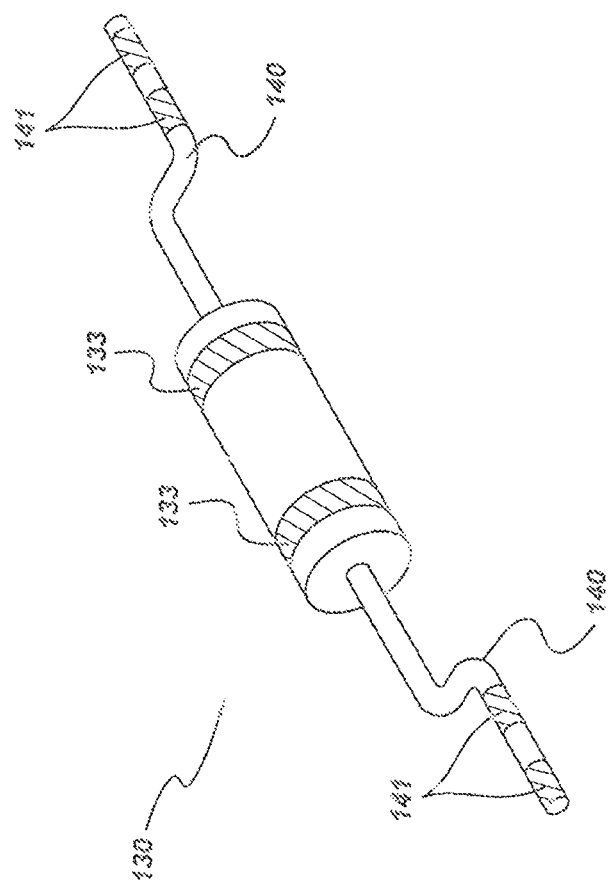
FIG. 4 shows an example of a microstimulator with one or more leads coupled thereto according to principles described herein.

FIG. 4 shows an example of a microstimulator 130 with one or more leads 140 coupled thereto. As shown in FIG. 4, each of the leads 140 may include one or more electrodes 141 disposed thereon. As shown in FIG. 4, the microstimulator 130 may additionally or alternatively include one or more leadless electrodes 133 disposed on the outer surface thereof.

Figure 5:
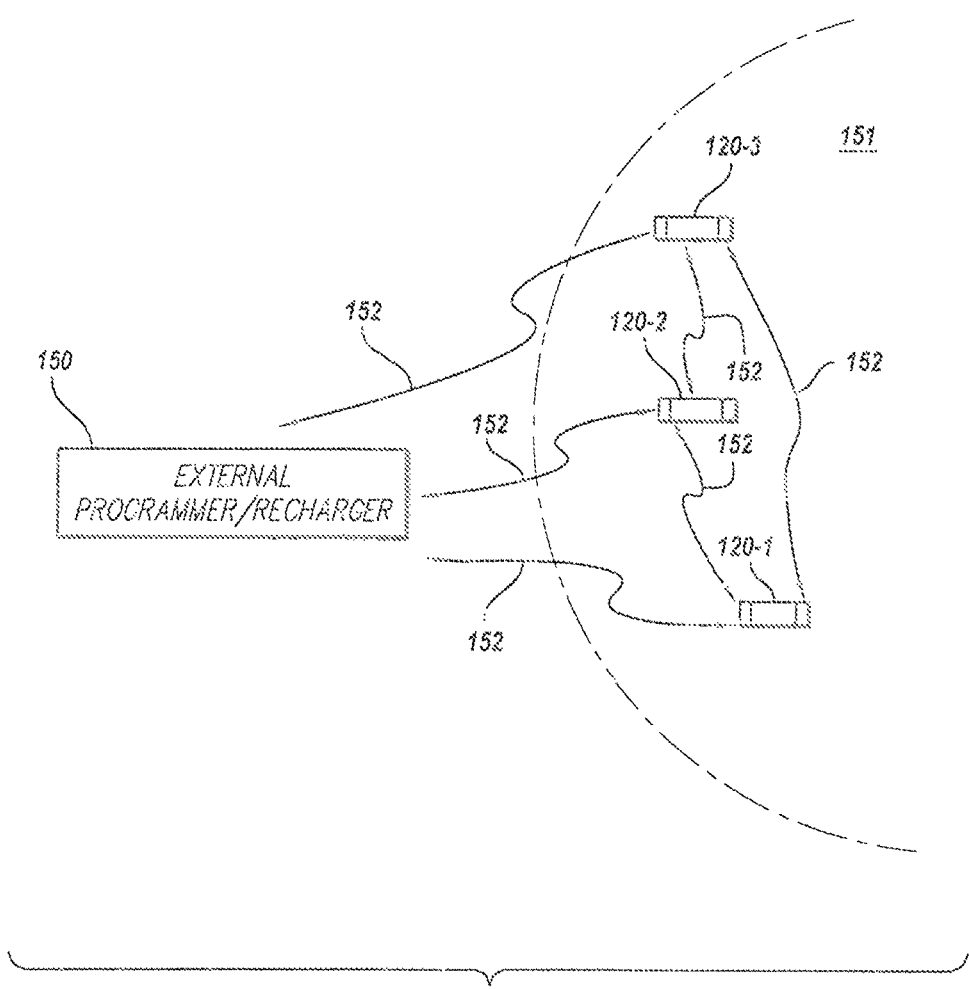
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of the symptoms or causes of a particular medical condition and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators of a particular medical condition, communicate or receive data regarding such indicators, and adjust stimulation parameters accordingly.

In order to determine the strength and/or duration of electrical stimulation and/or amount and/or type(s) of stimulating drug(s) required to most effectively treat a particular medical condition, various indicators of the medical condition and/or a patient's response to treatment may be sensed or measured. The stimulator 120 may then adjust the stimulation parameters (e.g., in a closed loop manner) in response to one or more of the sensed indicators. Exemplary indicators include, but are not limited to, electrical activity of the brain (e.g., via electroencephalography (EEG)), neurotransmitter levels, hormone levels, metabolic activity in the brain, blood flow rate, medication levels within the patient, patient input, temperature of the stimulation site, physical activity level, brain hyperexcitability, indicators of collateral tissue stimulation, and/or muscle tone in neck (e.g., mechanical strain, pressure sensor, electromyography (EMG)). In some examples, the stimulator 120 may be configured to perform the measurements. Alternatively, other sensing devices may be configured to perform the measurements and transmit the measured values to the stimulator 120. Exemplary sensing devices include, but are not limited to, chemical sensors, electrodes, optical sensors, mechanical (e.g., motion, pressure) sensors, and temperature sensors.

Thus, one or more external devices may be provided to interact with the stimulator 120, and may be used to accomplish at least one or more of the following functions:

Function 1: If necessary, transmit electrical power to the stimulator 120 in order to power the stimulator 120 and/or recharge the power source 125.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional functions may include adjusting the stimulation parameters based on information sensed by the stimulator 120 or by other sensing devices.

As mentioned, one or more stimulation sites within a patient may be stimulated by a stimulator 120 to treat a variety of different medical conditions. For example, it is believed that stimulation of one or more of me occipital nerves may be effective in treating headache. Additional or alternative stimulation sites within the head and/or neck that may be stimulated in order to treat headache include, but are not limited to, one or more of the cranial nerves, the trigeminal nerve, the infraorbital nerve, the facial nerve, the maxillary nerve, the mandibular nerve, and branches thereof.

Hence, as will be described in more detail below, one or more leads 121 with one or more electrodes 122 disposed thereon may be implanted within a patient such that the electrodes 122 are in communication with one or more stimulation sites within the patient. As used herein, the term in communication with" refers to the electrodes 122 being adjacent to, in the general vicinity of, in close proximity to, directly next to, or directly on the stimulation site. For example, with reference to FIGS. 1B and 1C, the one or more leads 121 may be implanted in the patient's neck at or near the base of the skull, at the back of the head, on the top or superior portion of the skull, or at any other suitable location.

However, one of the issues with using a stimulator 120 with one or more leads 121 coupled thereto to stimulate a stimulation site within a patient is lead migration. For example, an implantable stimulator 120 and its associated lead(s) 121 are generally implanted on a long-term or permanent basis. However, with time and with the natural movement of the patient, a lead 121 coupled to an implanted stimulator 120 may move away from the location where it was first implanted. For example, a simple nod of the head may cause a lead 121 that is not securely implanted within the neck to shift positions. Likewise, twisting of the torso may cause a lead 121 that is not securely implanted within the back to shift positions. This tendency to move is known as lead migration, or simply, migration.

Figure 6:
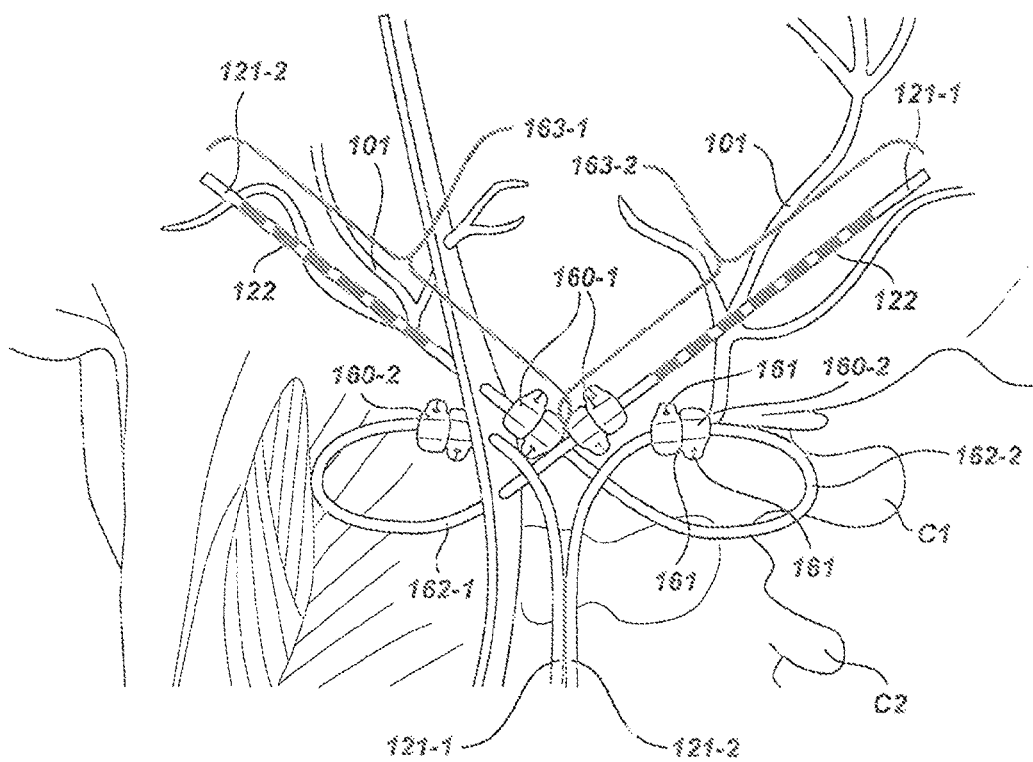
FIG. 6 illustrates an exemplary lead configuration according to principles described herein.

Hence, the systems and methods described herein may be used to minimize and/or eliminate lead migration. FIG. 6 illustrates an exemplary lead configuration wherein multiple leads 121 with a number of electrodes 122 disposed on a distal portion 163 thereof are implanted such that one or more of the electrodes 122 are in communication with one or more of the occipital nerves 100. The number of electrodes 122 disposed on each lead 121 may vary as may serve a particular application and lead size.

In some examples, as will be described in more detail below, each electrode 122 may be selectively programmed to have a positive (anode), negative (cathode), or OFF polarity to create a particular stimulation field when current is applied. Thus, different combinations of programmed anode and cathode electrodes 122 may be used to deliver a variety of current waveforms at one or more stimulation sites. Moreover, any of the other stimulation parameters (e.g., frequency, pulse width, amplitude, burst pattern, duty cycle, ramp on time, and ramp off time) of the stimulation current delivered by each of the electrodes 122 may be individually programmed. In this manner, as will be described in more detail below, current steering (also referred to as neuronavigation or e-trolling) may be used after the leads 121 are implanted to tailor the stimulation to the needs of a particular patient.

As shown in FIG. 6, the lead configuration may include two leads (e.g., 121-1 and 121-2, collectively referred to herein as 121). In this example, a distal portion 163-1 of the first lead 121-1 is positioned over the greater occipital nerve 101-1 on the right side of the patient and a distal portion 163-2 of the second lead 121-2 is placed over the greater occipital nerve 101-2 on the left side of the patient. The distal portions 163 of the leads 121 shown in FIG. 6 and in the other examples described herein are straight for illustrative purposes only. It will be recognized that the distal portions 163 may alternatively be curved, helical, paddle-shaped, or of any other shape as may serve a particular application.

The distal portions 163 of each of the leads 121 shown in FIG. 6 cover the greater occipital nerves 101 for illustrative purposes only. It will be recognized that the leads 121 may be located at any other stimulation site (e.g., the lesser occipital nerve 102) as may serve a particular application. In some examples, the distal tip of each of the leads 121 is placed four to five centimeters from the midline (i.e., the medial line or plane of the body) to minimize the need to advance the leads 121 following insertion. However, it will be recognized that the leads 121 may be placed any distance from the midline.

Configurations having two leads 121, such as the configuration shown in FIG. 6, are advantageous in applications wherein it is desirable to apply electrical stimulation to multiple stimulation sites. For example, the lead configuration of FIG. 6 may be used to simultaneously apply electrical stimulation to locations on both the right and left sides of the patient. However, it will be recognized that a single lead 121 or more than two leads 121 may be used in accordance with the systems and methods described herein.

The leads 121 are shown in FIG. 6 to be implanted over the patient's neck at or near the base of the skull in the C1 region. The leads 121 may additionally or alternatively be implanted over the scalp of the patient or at any other suitable location.

Figure 7A:
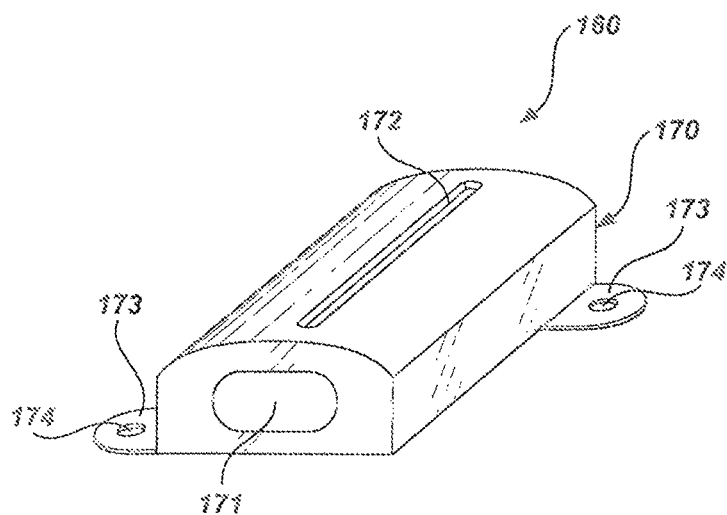
FIG. 7A is a perspective view of an exemplary suture sleeve according to principles described herein.
Figure 7B:
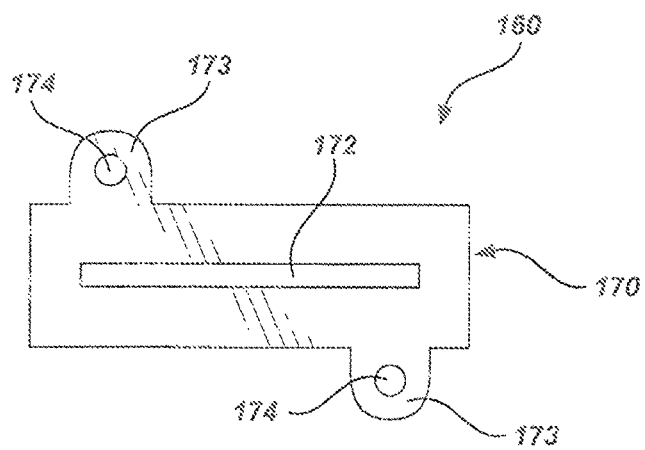
FIG. 7B is a top view of the suture sleeve illustrated in FIG. 7A according to principles described herein.

A number of suture sleeves 160 may be used to help minimize or eliminate migration of the leads 121 within the patient. FIG. 7A is a perspective view of an exemplary suture sleeve 160 that may be used in accordance with the systems and methods described herein. FIG. 7B is a top view of the suture sleeve 160 illustrated in FIG. 7A. As shown in FIG. 7A, the suture sleeve 160 includes a main body 170 with a lumen 171 extending therethrough. The lumen 171 is dimensioned so as to allow passage therethrough of one of the leads 121.

As shown in FIGS. 7A-7B, one or more slits 172 may be included along the main body 170 of the suture sleeve 160 through which an adhesive may be inserted into the lumen 171 to secure the lead 121 to the suture sleeve 160. In some examples, the adhesive may initially be in a liquid state and solidify upon being inserted into the lumen 171. In this manner, the adhesive may be configured to minimize the risk of lead slippage or migration. Any suitable surgical adhesive may be used including, but not limited to, cyanoacrylate, Duraseal™, TRUFILLO® n-BCA, BioGlue™ Surgical Adhesive, Tisseal, Fibrin, and any type of adhesive silicone.

The slit 172 also serves to prevent bunching as a suture is tied around the main body 170 of the suture sleeve 160. The suture that is tied around the main body 170 of the suture sleeve 160 will be described in more detail below.

FIGS. 7A-7B show that the suture sleeve 160 may also include a number of wing members 173 extending away from the main body 170. Each of the wing members 173 may include a hole 174 through which a suture can be sewn to secure the suture sleeve 160 in place, for example, to fascia. The suture sleeve 160 shown in FIGS. 7A-7B includes two wing members 173 for illustrative purposes only. It will be recognized that any number of wing members 173 may be included through which sutures may be sewn to anchor the suture sleeve 160 in place. Additionally or alternatively, the suture sleeve 160 may include one or more anchors, hooks, adhesives, or other securing devices that are configured to secure the suture sleeve 160 in place.

Figure 7C:
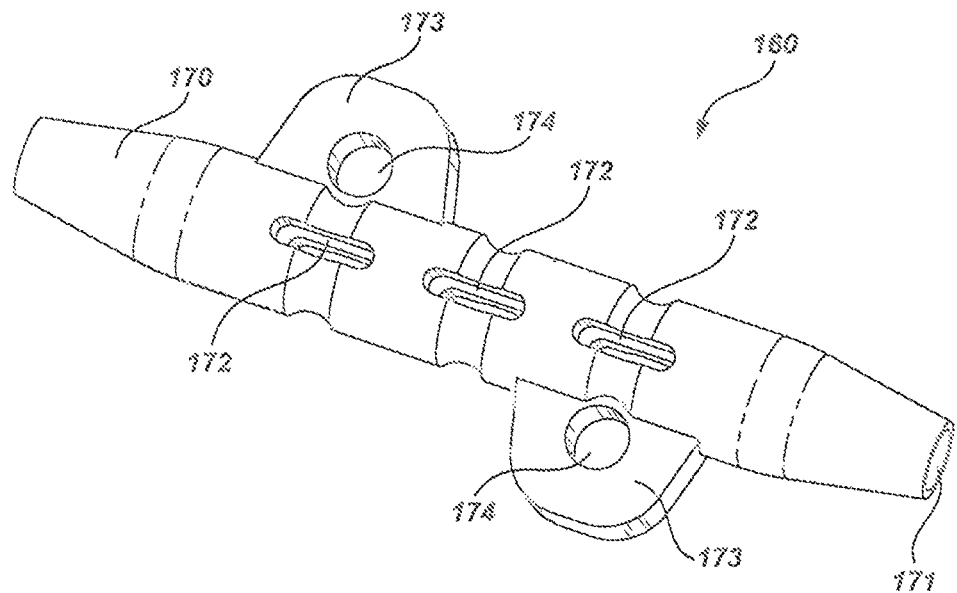
FIGS. 7C-7D show perspective views of additional exemplary suture sleeves according to principles described herein.
Figure 7D:
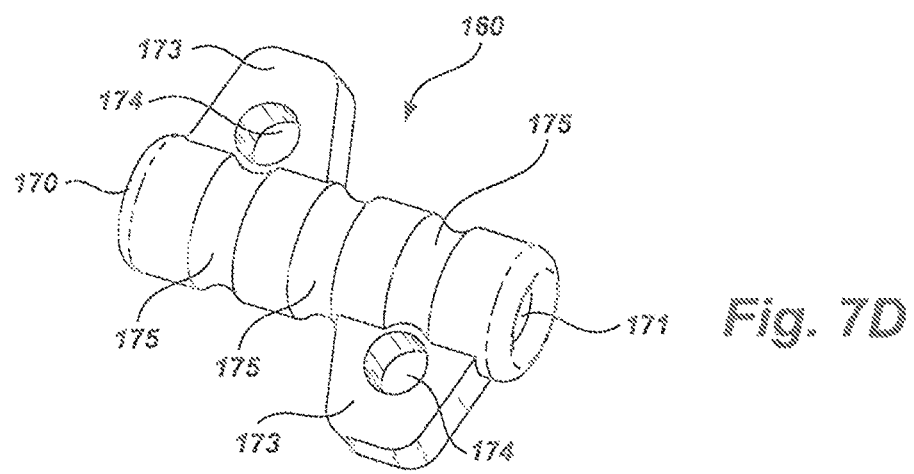

FIGS. 7C-7D show variations of the suture sleeves 160 that may be used in connection with the systems and methods described herein. For example, as shown in FIG. 7C, the suture sleeve 160 may be generally cylindrically shaped and include multiple slits 172 extending therethrough. Additionally or alternatively, as shown in FIG. 7D, the suture sleeve 160 may include a number of grooves 175 disposed on its main body 170. These grooves 175 may be configured to guide and retain placement of one or more sutures that are used to secure the lead 121 in place. It will be recognized the suture sleeves 160 may include additional or alternative features as may serve a particular application.

Returning to FIG. 6, each lead 121 is secured by one or more suture sleeves 160—e.g., a distal suture sleeve 160-1 and a proximal suture sleeve 160-2. The proximal suture sleeve 160-2 is closer to the stimulator (not shown) than is the distal suture sleeves 160-1. It will be recognized that any number of suture sleeves 160 may be used to secure the leads 121 in place. Moreover, it will be recognized that any other securing device may additionally or alternatively be used to secure the leads 121 in place. Such securing devices may include, but are not limited to, one or more sutures, hooks, adhesives, or anchors.

Each suture sleeve 160 may be sutured into place using one or more sutures 161. In some examples, the sutures are non-absorbable. Exemplary non-absorbable sutures that may be used to suture the suture sleeves 160 into place include, but are not limited to, a braided nylon (e.g., Nurolon), a braided polyester (e.g., Ethibond or Mersiline), Prolene, Surgilene, Tevdek, a polypropylene material, a braided polyester material, and a Teflon coated polyester material.

In some examples, at least two sutures 161 are used to affix a particular suture sleeve 160 to fascia. These sutures 161 may be threaded through the holes 174 that are a part of the wing members 173. At least one additional suture 161 may be cinched around the main body 170 of the suture sleeve 160 to prevent slippage of the lead 121 within the suture sleeve 160. Although three sutures 161 are illustrated as affixing each suture sleeve 160 in FIG. 6, it will be recognized that any number of sutures 161 may be used to affix each suture sleeve 160 as may serve a particular application.

In some examples, each distal suture sleeve 160-1 may be sutured or otherwise fixed to fascia or any other securing site that is located in the same rostro-caudal motion segment as the most proximal electrode 122 on the lead 121 to minimize relative movement between the target stimulation site (e.g., the greater occipital nerve 101) and the distal suture sleeve 160-1. For example, if the most proximate electrode 122 to the distal suture sleeve 160-1 is located in the C2 region, the distal suture sleeve 160-1 is sutured to fascia in the same C2 region. Likewise, if the most proximate electrode 122 to the distal suture sleeve 160-1 is located in the scalp region, the distal suture sleeve 160-1 is sutured to fascia overlying the scalp.

As shown in FIG. 6, the long axis of each distal suture sleeve 160-1 is substantially collinear with the long axis of the electrode region of its corresponding lead 121. Each lead 121 passes through the lumen 171 of its corresponding distal suture sleeve 160-1 and then forms a loop (e.g., 162-1 and 162-2, collectively referred to herein as 162) of at least 360 degrees. To this end, the leads 121 are configured to pass through corresponding proximal sleeves 160-2, which are positioned so as to maintain the shape of the loops 162. The leads 121 may then be routed to the stimulator (not shown). The portion of the leads 121 that makes up each loop 162 may be made out of any flexible material.

The loops 162 are configured to minimize the forces that are exerted on the distal and proximal sutures sleeves 160-1 and 160-2 when the patient moves his or her head. Hence, the loops 162 are also referred to as "force redirection loops" herein. The force redirection loops 162 are also configured to minimize lead migration. Hence, the force redirection loops 162 may be dimensioned and aligned such that there are minimal forces on either the distal or proximal suture sleeve 160-1 or 160-2.

In some examples, each lead 121 crosses the midline prior to forming its corresponding force redirection loop 162. For example, as shown in FIG. 6, the electrode portion of lead 121-1 is located on the right side of the midline. The lead 121-1 crosses the midline prior to forming force redirection loop 162-1. Lead 121-2 also crosses the midline prior to forming force redirection loop 162-2. Hence, the leads 121 cross each other prior to forming force redirection loops 162. Alternatively, as will be described in more detail below, the leads 121 may be positioned such that they form force redirection loops 162 without crossing each other.

As mentioned, each lead 121 passes through a corresponding proximal suture sleeve 160-2 in forming a force redirection loop 162. As shown in FIG. 6, the long axis of each proximal suture sleeve 160-2 may be substantially perpendicular to the midline or spine. This placement minimizes lead migration that may be caused by the flexion or extension of the neck. Such flexion or extension of the neck may cause the proximal suture sleeve 160-2 to bend, however, the risk of the lead 121 slipping within the suture sleeve 160-2 is minimized when the proximal suture sleeve 160-2 is perpendicular to the midline or spine. Alternatively, as will be described in more detail below, the long axis of the proximal suture sleeve 160-2 may be oriented in any non-parallel direction with respect to the midline.

After the leads 121 pass through corresponding proximal suture sleeves 160-2, the leads 121 are routed to a stimulator 120. In some examples, as will be described in more detail below, the leads 121 may form one or more additional loops prior to being coupled to the stimulator 120. It will be recognized that one or more devices, such as the stimulator 120, may be implanted in any suitable location within the body. For example, the stimulator 120 may be implanted above the iliac crest or over the ribcage to minimize the path of the leads 121 and to minimize the need for multiple lead extensions. Other exemplary implant locations may include, but are not limited to, the buttocks, the neck, the brain, the skull, a subcutaneous area in communication with the skull, or any other suitable location within the patient.

Figure 8:
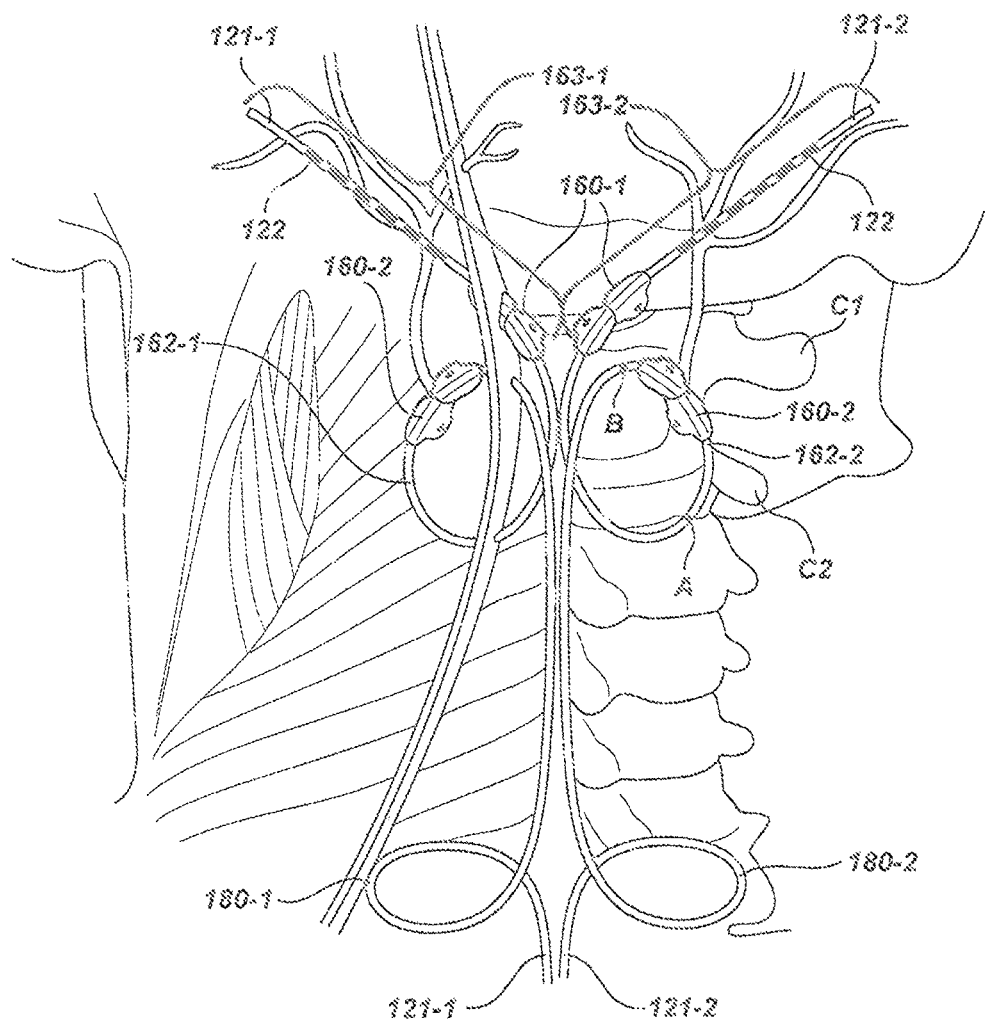
FIG. 8 illustrates another exemplary lead configuration according to principles described herein.

FIG. 8 illustrates an alternative lead configuration that may be used in connection with the systems and methods described herein. The lead configuration of FIG. 8 is similar to that described in connection with FIG. 6 in that the configuration includes multiple leads 121 and suture sleeves 160 configured to secure the leads 121 in place. The leads 121 may each include one or more electrodes 122 disposed thereon and are implanted such that one or more of the electrodes 122 are in communication with one or more stimulation sites (e.g., the greater occipital nerves 101).

As shown in FIG. 8, each distal suture sleeve 160-1 may be substantially collinear with the long axis of the distal portion 163 of its corresponding lead 121. Each distal suture sleeve 160-1 is sutured or otherwise fixed to fascia or any other securing site that is located, for example, in the same vertebral level as the most proximal electrode 122 on the lead 121 to minimize relative movement between the target stimulation site (e.g., the greater occipital nerve 101) and the distal suture sleeve 160-1. For example, if the most proximate electrode 122 to the distal suture sleeve 160-1 is located in the C2 region, the distal suture sleeve 160-1 is sutured to fascia in the same C2 region. Likewise, if the most proximate electrode 122 to the distal suture sleeve 160-1 is located in the scalp region, the distal suture sleeve 160-1 is sutured to fascia overlying the scalp.

As described previously in connection with the example of FIG. 6, each lead 121 passes through the lumen 171 of its corresponding distal suture sleeve 160-1 and then forms a force redirection loop (e.g., 162-1 and 162-2) of at least 360 degrees before passing through the proximal sleeves 160-2. However, as shown in the example of FIG. 8, each lead 121 forms the force redirection loop 162 without crossing the other lead 121. For example, lead 121-1 forms force redirection loop 162-1 without crossing lead 121-2. In some examples, each lead 121 forms a force redirection loop 162 without crossing the midline.

As shown in FIG. 8, proximal suture sleeves 160-2 may be provided through which the leads 121 pass. In some examples, each proximal suture sleeve 160-2 may be located at a securing site having a position that is greater than or equal to substantially 180 degrees but less than or equal to substantially 315 degrees along its corresponding force redirection loop 162 as measured from the securing site of its distal suture sleeve 160-1.

To illustrate, a point along the force redirection loop 162-2 corresponding to approximately 180 degrees from the loop's corresponding distal suture sleeve 160-1 is labeled "A". Likewise, a point along the force redirection loop 162-2 corresponding to approximately 315 degrees from the loop's corresponding distal suture sleeve 160-1 is labeled "B". Hence, the proximal suture sleeve 160-2 corresponding to the force redirection loop 162-2 shown in FIG. 8 is located in between points A and B.

In some examples, the long axis of each proximal suture sleeve 160-2 is aligned so as to maintain a curve in its corresponding lead 121 of at least 45 degrees between the proximal suture sleeve 160-2 and the stimulator 120. As used herein, the term "maintain a curve" and variations thereof mean ensuring that a curve of at least 45 degrees persists even if the lead 121 is pulled taut between the proximal suture sleeve 160-2 and the stimulator 120. In this manner, the risk of the lead 121 slipping within the suture sleeves 160 is minimized. In some particular examples, the long axis of each proximal suture sleeve 160-2 is aligned so as to maintain a curve in its corresponding lead 121 of at least 90 degrees between the proximal suture sleeve 160-2 and the stimulator 120.

To illustrate an example of this, FIG. 8 shows a configuration wherein each proximal suture sleeve 160-2 is located at a point along its corresponding force redirection loop 162 such that the lumen of each proximal suture sleeve 160-2 is substantially perpendicular to the distal portion 163 of its corresponding lead 121, and thus is also substantially perpendicular to the lumen of its corresponding distal suture sleeve 160-1. Such a configuration may be used to maintain a curve in the leads 121 of at least 45 degrees between the proximal suture sleeves 160-2 and the stimulator 120.

In some examples, the proximal suture sleeves 160-2 are placed caudal to C1 to avoid undesirable suturing over the stimulation site (e.g., the greater occipital nerve 101).

After passing through the proximal suture sleeves 160-2, the leads 121 may each be formed into one or more additional loops (e.g., 180-1 and 180-2, collectively referred to herein as 180) prior to being routed to the stimulator 120. These additional loops 180 may relieve strain that may be placed on the leads 121 by changing size as the patient moves. Hence, these additional loops 180 are referred to herein as "strain relief loops" for illustrative purposes.

FIG. 8 shows that the strain relief loops 180 may be formed at the base of the neck. Additionally or alternatively, the strain relief loops 180 may be formed at any other suitable location as may serve a particular application.

In some examples, the strain relief loops 180 are located within a pocket made by a surgeon in the subcutaneous fat and are not sutured or otherwise affixed to tissue. In this manner, the fat retains the general shape of the strain relief loops 180 while allowing the loops 180 to vary in size as the patient moves.

Additionally or alternatively, the leads 121 may each form a strain relief loop at or near the location of the stimulator 120. For example, if the stimulator 120 is implanted over the ribcage, lead(s) 121 may form one or more strain relief loops at or near the rib cage just prior to being coupled to the stimulator 120.

FIGS. 9A-9E illustrate a number of alternative lead configurations that may be used in connection with the systems and methods described herein. As will be described in more detail below, each lead configuration shown in FIGS. 9A-9E may include at least one lead 121 having at least two curves of opposite concavity in between the distal and proximal suture sleeves 160-1 and 160-2. The at least two curves of opposite concavity may also be referred to as an "s-curve" in the examples given herein. As will be described in more detail below, the s-curve may be configured to minimize and/or eliminate lead migration. It will be recognized that the lead configurations shown in FIGS. 9A-9E are merely illustrative of the many different configurations that may include one or more s-curves and that the configurations may be applied to any type of stimulating member (e.g., one or more catheters). Moreover, it will be recognized that the lead configurations shown in FIGS. 9A-9E may be used to apply a stimulus to any stimulation site within a patient.

Figure 9A:
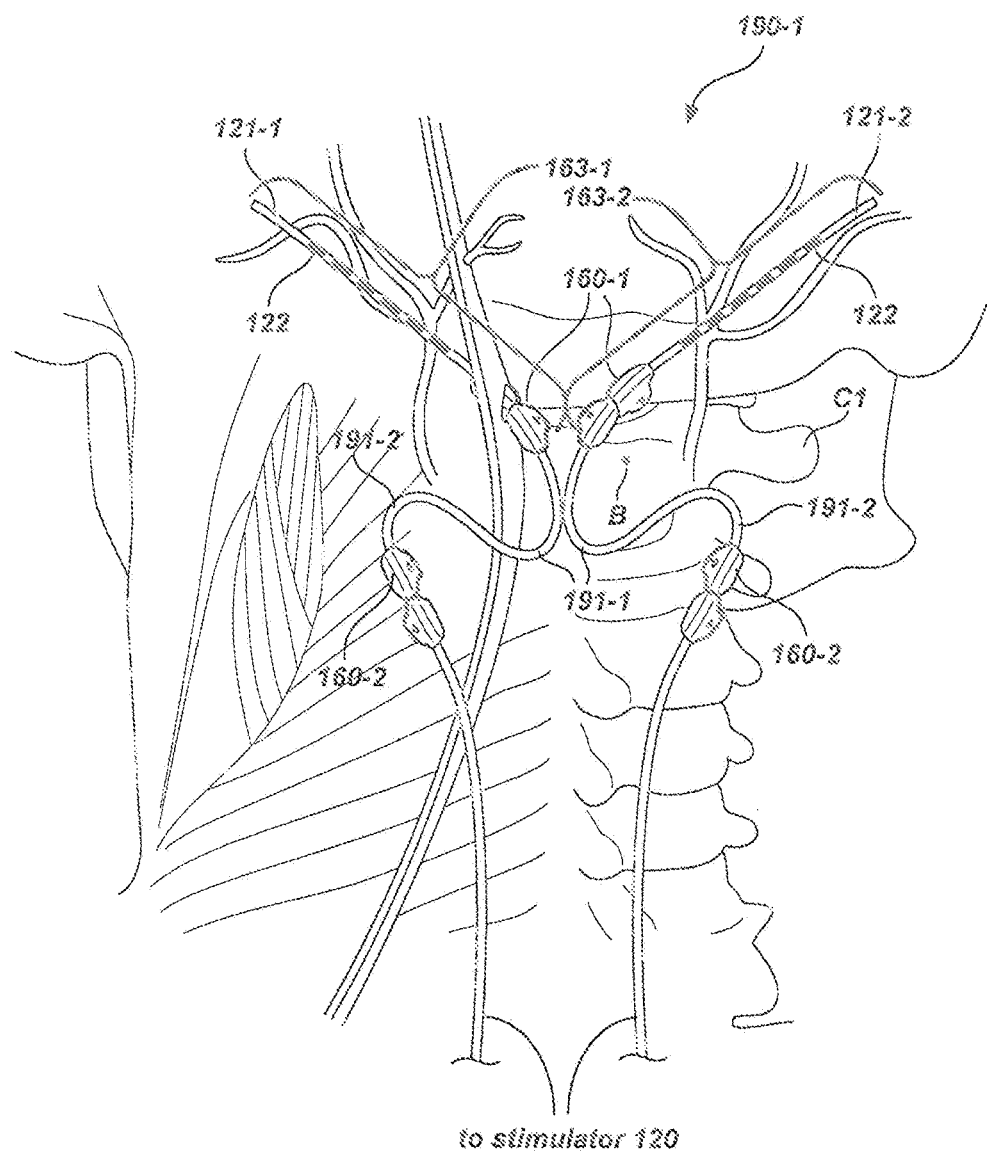
FIGS. 9A-9E illustrate a number of s-curve lead configurations according to principles described herein.

FIG. 9A shows a first s-curve configuration 190-1 that may be used in connection with the systems and methods described herein. As shown in FIG. 9A, a distal portion 163 of each lead 121 may be positioned such that the distal portion 163 is in communication with one or more stimulation sites (e.g., the greater occipital nerves 101). Each distal portion 163 may be secured at a first securing site with a distal suture sleeve 160-1. In some examples, as shown in FIG. 9A, the distal suture sleeves 160-1 may each be substantially collinear with the long axis of the distal portion 163 of its corresponding lead 121.

In some examples, each distal suture sleeve 160-1 may sutured or otherwise fixed to fascia or any other securing site that is located, for example, in the same vertebral level as the most proximal electrode 122 on the lead 121 to minimize relative movement between the target stimulation site (e.g., the greater occipital nerve 101) and the distal suture sleeve 160-1. For example, if the most proximate electrode 122 to the distal suture sleeve 160-1 is located in the C2 region, the distal suture sleeve 160-1 is sutured to fascia in the same 02 region. Likewise, if the most proximate electrode 122 to the distal suture sleeve 160-1 is located in the scalp region, the distal suture sleeve 160-1 is sutured to fascia overlying the scalp.

Each lead 121 may be configured to pass through the lumen 171 of its corresponding distal suture sleeve 160-1 and then form at least two curves of opposite concavity out of a proximal portion thereof. For example, FIG. 9A shows that each lead 121 may include a first curve 191-1 having a first concavity and a second curve 191-2 having a second concavity opposite that of the first. This s-curve configuration may be configured to minimize and/or eliminate lead migration and thereby facilitate stimulation of various stimulation sites within the body that may be affected by patient movement.

Each lead 121 may then pass through a proximal suture sleeve 160-2. The proximal suture sleeves 160-2 may be configured to secure the leads 121 at a securing site selected such that the first and second curves 191-2 and 191-2 of the leads 121 are located in between the distal and proximal suture sleeves 160-1 and 160-2.

After passing through the proximal suture sleeves 160-2, the leads 121 may each be routed to an implant site of the stimulator 120 and coupled to the stimulator 120 such that the stimulator 120 may apply a stimulus via one or more of the leads 121. In some examples, the leads 121 may be formed into one or more additional loops and/or s-curves as described above prior to being routed to the stimulator 120. Additionally or alternatively, the leads 121 may each form one or more loops and/or s-curves at or near the location of the stimulator 120. For example, if the stimulator 120 is implanted over the ribcage, lead(s) 121 may form one or more strain relief loops at or near the rib cage just prior to being coupled to the stimulator 120.

In some examples, each lead 121 shown in FIG. 9A may be located entirely on one side of the midline. For example, lead 121-1 is shown to be located entirely to the left of the midline, and lead 121-2 is shown to be located entirely to the right of the midline. It will be recognized, however, that one or more of the leads 121 may cross the midline at any point as may serve a particular application.

Figure 9B:
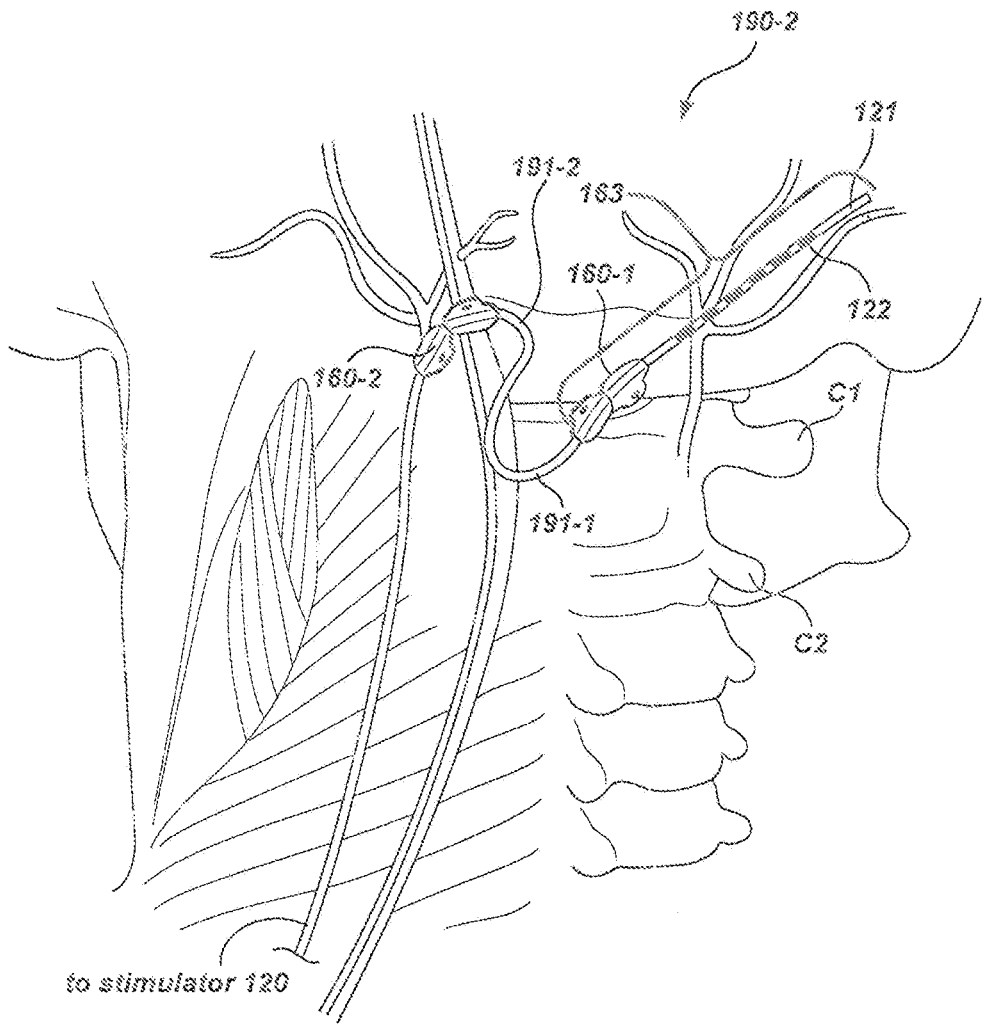

FIG. 9B illustrates another s-curve configuration 190-2 that may be used in connection with the systems and methods described herein. As shown in FIG. 9B, the s-curve configuration 190-2 includes a single lead 121. Multiple leads 121 may alternatively be used in s-curve configuration 190-2 as may serve a particular application.

As shown in FIG. 9B, a distal portion 163 of lead 121 may be positioned such that the distal portion 163 is in communication with one or more stimulation sites (e.g., the greater occipital nerves 101). Distal portion 163 may be secured at a first securing site with a distal suture sleeve 160-1. The lead 121 may be configured to pass through the lumen 171 of distal suture sleeve 160-1 and then form at least two curves of opposite concavity out of a proximal portion thereof. For example, FIG. 9A shows that lead 121 may include a first curve 191-1 having a first concavity and a second curve 191-2 having a second concavity opposite that of the first.

The lead 121 may then pass through a proximal suture sleeve 160-2. The proximal suture sleeves 160-2 may be configured to secure the lead 121 at a securing site selected such that the first and second curves 191-2 and 191-2 of the lead 121 are located in between the distal and proximal suture sleeves 160-1 and 160-2. After passing through the proximal suture sleeve 160-2, the lead 121 may be routed to an implant site of the stimulator 120 and coupled to the stimulator 120 in a manner similar to that described above. Multiple leads 121 may alternatively be used in an s-curve configuration similar to that shown in FIG. 9B as may serve a particular application.

Figure 9C:
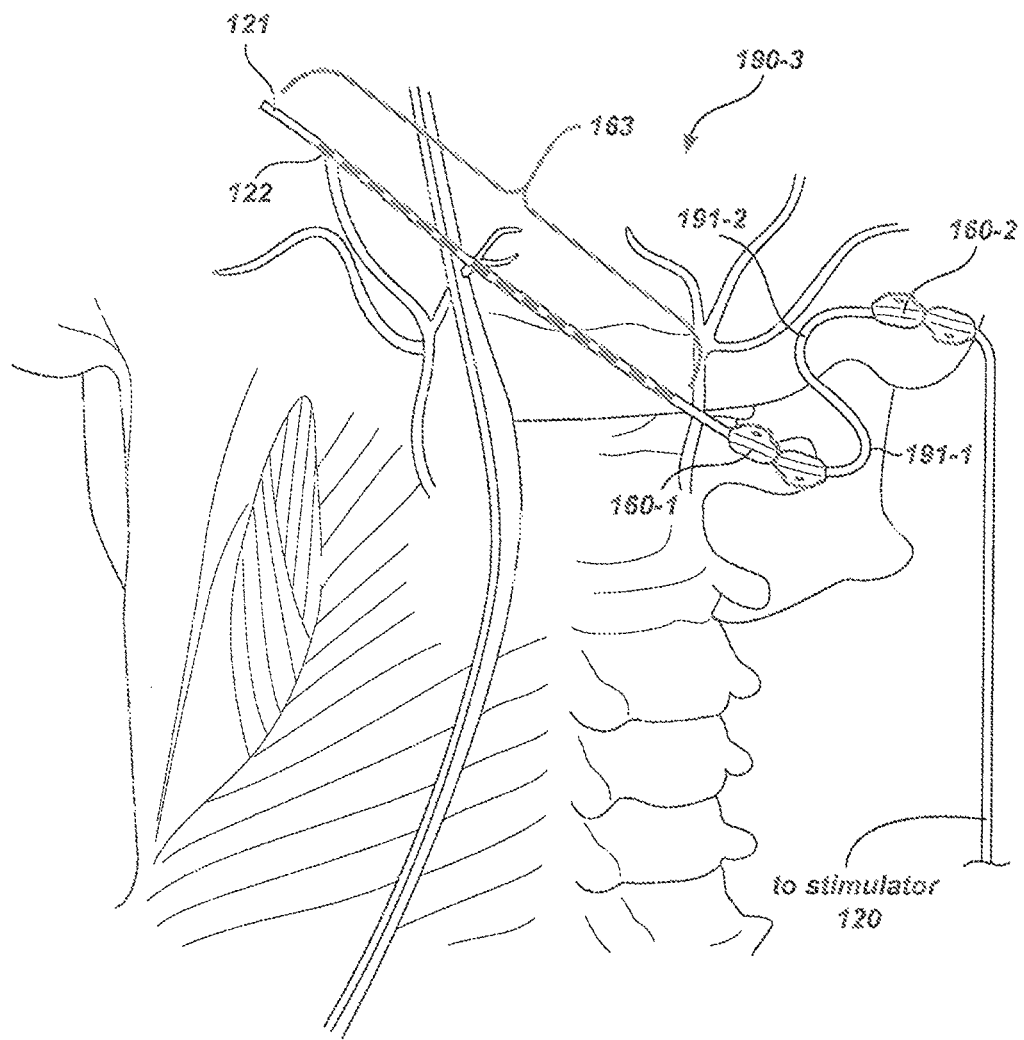

FIG. 9C illustrates another s-curve configuration 190-3 that may be used in connection with the systems and methods described herein. As shown in FIG. 9C, the s-curve configuration 190-3 includes a single lead 121 configured to be applied stimulation to stimulation sites located on either side of the midline.

As shown in FIG. 9C, the lead 121 may be secured by distal and proximal suture sleeves 160-1 and 160-2 in a similar manner to that described above. The portion of the lead 121 located in between the suture sleeves 160 may include a first curve 191-1 having a first concavity and a second curve 191-2 having a second concavity opposite that of the first. The lead 121 may then be routed to an implant site of the stimulator 120 and coupled to the stimulator 120 in a manner similar to that described above.

Figure 9D:
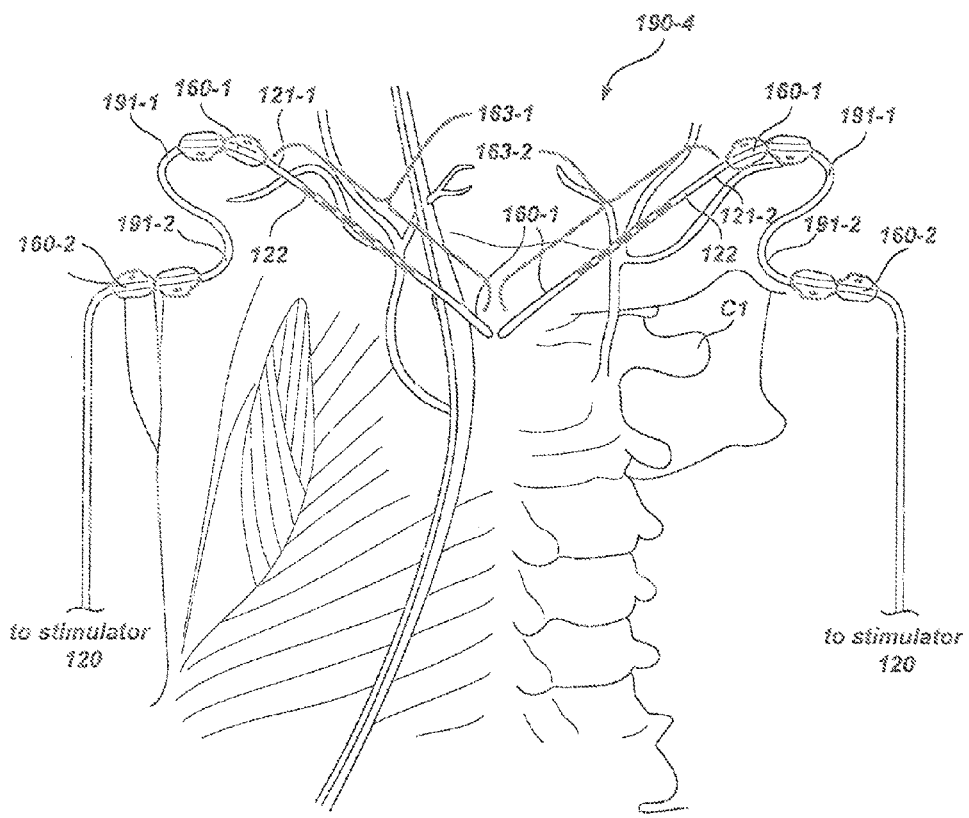

FIG. 9D illustrates another s-curve configuration 190-4 that may be used in connection with the systems and methods described herein. As shown in FIG. 9D, the s-curve configuration 190-4 includes leads 121-1 and 121-2 oriented such that the distal portions 163 thereof are directed downwards towards the stimulation sites. The leads 121 may each be secured by distal and proximal suture sleeves 160-1 and 160-2 in a similar manner to that described above. The portion of the leads 121 located in between the suture sleeves 160 may each include a first curve 191-1 having a first concavity and a second curve 191-2 having a second concavity opposite that of the first. The leads 121 may then be routed to an implant site of the stimulator 120 and coupled to the stimulator 120 in a manner similar to that described above.

Figure 9E:
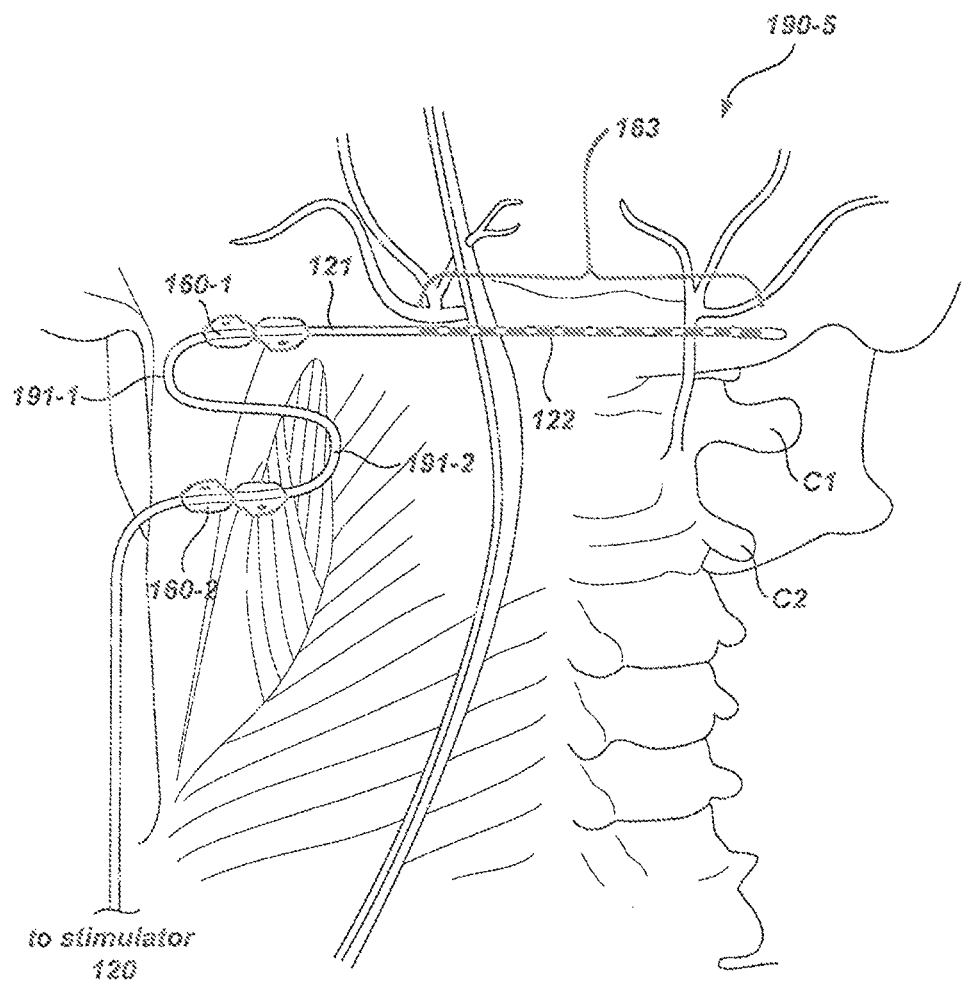

FIG. 9E illustrates another s-curve configuration 190-5 that may be used in connection with the systems and methods described herein. As shown in FIG. 9E, the s-curve configuration 190-5 includes a single lead 121 positioned substantially perpendicular to the midline. In this manner, the lead 121 may be used to apply stimulation to one or more stimulation sites on either side of the midline.

The lead 121 may be secured by distal and proximal suture sleeves 160-1 and 160-2 in a similar manner to that described above. The portion of the lead 121 located in between the suture sleeves 160 may include a first curve 191-1 having a first concavity and a second curve 191-2 having a second concavity opposite that of the first. The lead 121 may then be routed to an implant site of the stimulator 120 and coupled to the stimulator 120 in a manner similar to that described above.

As shown in FIG. 9E, the distal and proximal suture sleeves 160-1 and 160-2 may be positioned substantially perpendicular to the midline of the patient. The suture sleeves 160 may be alternatively positioned in any other suitable manner.

Figure 10:
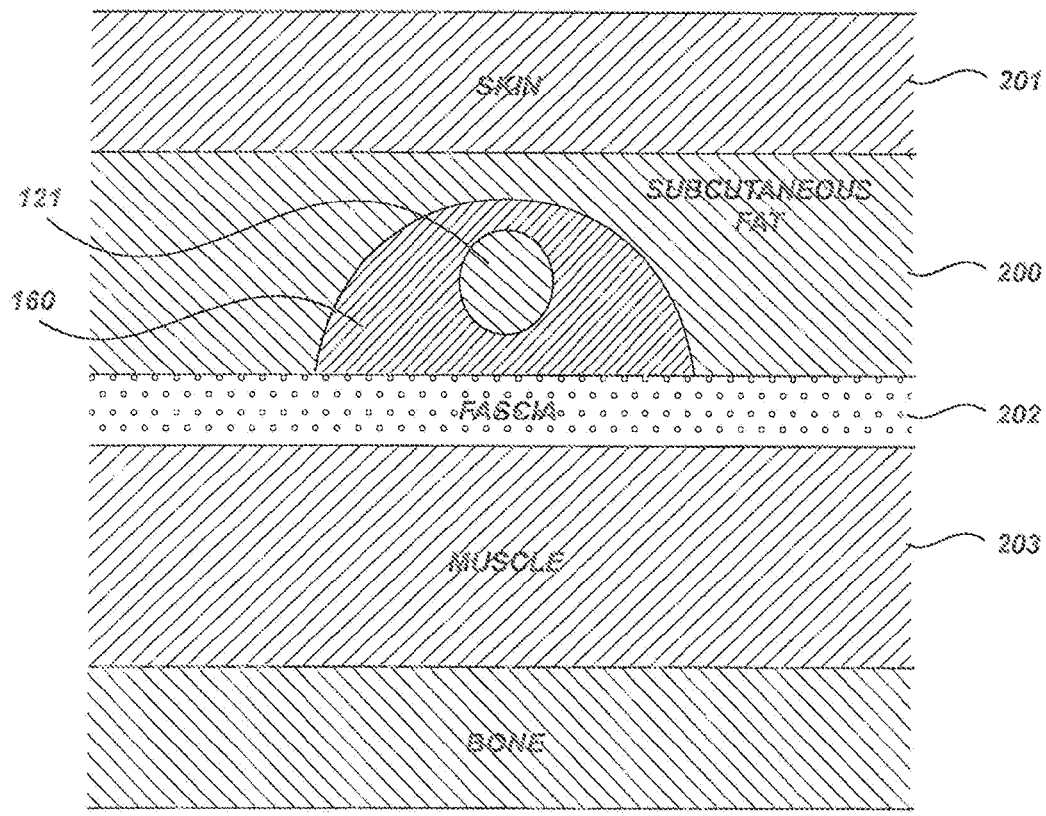
FIG. 10 is a cross-sectional view of an implanted suture sleeve according to principles described herein.

As mentioned, each suture sleeve 160 described herein may be affixed to fascia. FIG. 10 is a cross-sectional view of an exemplary implanted suture sleeve 160. As shown in FIG. 10, the suture sleeve 160 with a lead 121 disposed therethrough may be located within subcutaneous fat 200 located directly beneath the skin 201. The bottom surface of the suture sleeve 160 is coupled to the fascia 202, which is a thin layer of fibrous tissue that separates the subcutaneous fat 200 from muscle 203.

A number of methods may be used to locate the optimal implantation site for the leads 121. For example, an insulated regional nerve block needle or other probe may be used to identify the location of a desired nerve (e.g., the greater occipital nerve 101) prior to or during the implant procedure. The leads 121 may then be implanted such that the electrodes 122 disposed thereon are in communication with the desired nerve.

Additionally, the patient is often awake and under a local anesthesia for the implantation procedure. Consequently, obtaining verbal feedback from the patient as to the effect of a trial stimulation or various stimulation parameters may be useful in obtaining the most beneficial lead placement and stimulation current parameters. However, it is often difficult to hear the patient due to the orientation of the patient and the dressings used around the implantation procedure. Consequently, a microphone may be placed at or near the patient's mouth. The sound transduced by the microphone may be amplified and/or output through a speaker where it is clearly audible to the personnel performing the testing or implantation of the leads 121. Other patient feedback systems and methods may be used including, but not limited to, keypads, remote controls and other communication devices.

Once the leads 121 are implanted, current steering (also referred to as neuronavigation or e-trolling) may be used to tailor the stimulation to the needs of a particular patient. U.S. Pat. No. 6,393,325, which is incorporated herein by reference in its entirety, discloses an exemplary method of current steering that may be used in connection with the present methods and systems.

By way of example, another exemplary method of using current steering to optimize the stimulation parameters for a particular patient may be carried out according to the following sequence of procedures. For illustrative purposes only, it will be assumed in the example given below that it is desired to apply stimulation to one or more of the occipital nerves 130. The steps listed below may be modified, reordered, and/or added to as best serves a particular application.

1. Beginning with the most distal electrode 122 disposed on the left lead 121-2, steer down until the patient begins reporting paresthesias. Continue steering down one electrode at a time and identify where along the lead 121-2 the paresthesia is the highest and the most intense. Patient feedback and/or some other monitoring device may be used to signal where the paresthesia is the highest and most intense. Mark this location as the optimal stimulation location along this lead 121-2.

2. Repeat step 1 above for the right lead 121-1.

3. For each lead 121, evaluate the distance of the optimal electrode from the midline. If the distance is greater than 30 mm in the neck region, the optimal stimulation site is most likely the lesser occipital nerve 102.

4. If the optimal stimulation site found in step 3 is the lesser occipital nerve 102, repeat steps 1-3 to add a second stimulation site for both leads 121 which is less than 30 mm from the midline. This stimulation site covers the greater occipital nerve 101.

In some instances, it may be desirable to measure the amount of lead migration that occurs over a specific amount of time. For this purpose, a radioopaque bead may be implanted within the patient over the center of the occipital protuberance to provide a landmark in the radiographic plane of the leads. Alternatively the radioopaque bead may be affixed to the patient's skin. After the lead implant procedure is complete, a true AP fluoroscopic image of the leads 121 and the bead may be printed. Should lead migration be suspected in the future, a second x-ray may be taken with a bead over the occipital protuberance to allow quantitative assessment of lead migration.

Figure 11:
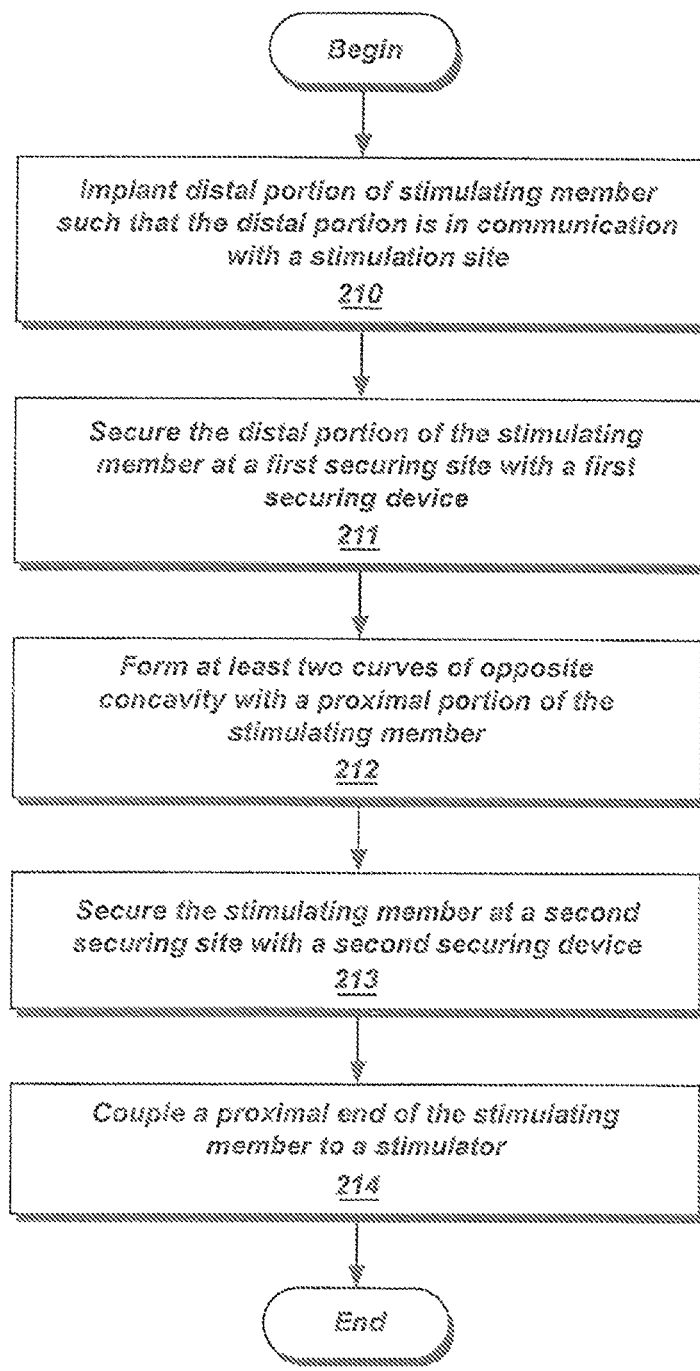
FIG. 11 is a flow chart illustrating an exemplary method of facilitating stimulation of one or more stimulation sites within a patient according to principles described herein.

An exemplary method of facilitating stimulation of one or more stimulation sites within a patient will now be given in connection with the flow chart of FIG. 11. The steps illustrated in FIG. 11 may be modified, reordered, and/or added to as may serve a particular application.

In step 210, a distal portion of a stimulating member (e.g., a lead or a catheter) is implanted such that the distal portion is in communication with a stimulation site located within a patient. The stimulation site may be located within the head, neck, spinal cord, or at any other location within the patient as may serve a particular application.

In step 211, the distal portion of the stimulating member is secured at a first securing site with a first securing device (e.g., a suture sleeve, a suture, an anchor, or any other suitable securing device). The distal portion of the stimulating member may secured in any of the ways described herein.

In step 212, at least two curves of opposite concavity are formed with a proximal portion of the stimulating member.

In step 213, the stimulating member is secured at a second securing site with a second securing device. In some examples, the location of the second securing site is selected such that the at least two curves of opposite concavity are positioned in between the first and second securing devices.

In step 214, a proximal end of the stimulating member is coupled to a stimulator. In some examples, the stimulator may be at least partially implanted within the patient. The stimulator may then apply a stimulus (e.g., electrical stimulation via one or more electrodes disposed on a lead or drug stimulation via a catheter) to the stimulation site.

The preceding description has been presented only to illustrate and describe embodiments of the invention. It is not intended to be exhaustive or to limit the invention to any precise form disclosed. Many modifications and variations are possible in light of the above teaching.

What is claimed as new and desired to be protected by Letters Patent of the United States:

1. A suture sleeve, comprising:
a body defining a lumen extending along the body and configured and arranged to receive a portion of a lead within the lumen,
a first groove disposed on the body of the suture sleeve;
a first wing member extending away from the body of the suture sleeve, and
a first hole disposed in the first wing member for suturing the suture sleeve to a securing site, wherein the first wing member intersects with the first groove and the first hole disposed in the first wing member is in an in-line alignment with the first groove.

2. The suture sleeve of claim 1, further comprising
a second groove disposed on the body of the suture sleeve;
a second wing member extending away from the body of the suture sleeve, and
a second hole disposed in the second wing member for suturing the suture sleeve to the securing site, wherein the second wing member intersects with the second groove and the second hole disposed in the second wing member is in an in-line alignment with the second groove.

3. The suture sleeve of claim 2, wherein the first and second wing members extend away from the body of the suture sleeve in opposite directions.

4. The suture sleeve of claim 3, wherein the first and second wing members are disposed in a staggered arrangement along a length of the suture sleeve.

5. The suture sleeve of claim 2, further comprising a third groove disposed on the body of the suture sleeve and between the first and second grooves.

6. The suture sleeve of claim 1, further comprising a first slit disposed in the body of the suture sleeve, wherein the first slit is bound on four sides by the body and extends from an exterior of the body to the lumen defined in the body.

7. The suture sleeve of claim 6, wherein the first slit intersects the first groove.

8. A system, comprising:
a lead; and
the suture sleeve of claim 1 which is configured and arranged to receive a portion of the lead.

9. The system of claim 8, wherein the system comprises a plurality of the suture sleeves.

10. The system of claim 8, further comprising a stimulator coupleable to the lead.

11. A method comprising:
implanting a distal portion of the lead within a patient adjacent to a stimulation site;
securing the lead to at least one securing site within the patient using at least one suture sleeve, wherein each of the at least one suture sleeve is the suture sleeve of claim 1; and
coupling a proximal end of the lead to a stimulator.

12. The method of claim 11, wherein the at least one suture sleeve is a plurality of suture sleeves and the at least one securing site is a plurality of securing sites, wherein each of the plurality of suture sleeves secures the lead to a different one of the plurality of securing sites.

13. The method of claim 11, further comprising securing the suture sleeve with a suture that passes through the first hole and along the first groove.

14. The method of claim 11, wherein securing the lead comprises forming a loop of at least 360 degrees with a portion of the lead and securing the loop using at least one of the at least one suture sleeve.

15. The method of claim 14, wherein the at least one suture sleeve comprises a first suture sleeve and a second suture sleeve and the at least one securing site comprises a first securing site and a second securing site, wherein securing the loop comprises securing the loop at the first and second securing sites along the loop using the first and second suture sleeves, respectively, wherein the second securing site is at least 180 degrees, but no more than 315 degrees, further along the loop from the first securing site.

16. The method of claim 11, wherein said stimulation site comprises at least one or more of a greater occipital nerve and a lesser occipital nerve.

17. The method of claim 11, wherein the lead comprises a catheter, and wherein the method further comprises delivering one or more drugs to the stimulation site via the catheter.

18. The method of claim 11, wherein the lead comprises one or more electrodes disposed thereon, and wherein the method further comprises applying a stimulus generated by the stimulator to the stimulation site via at least one of the one or more electrodes.

19. The method of claim 18, wherein applying a stimulus comprises applying the stimulus to treat a headache.

20. The method of claim 11, further comprising using current steering to identify at least one stimulation parameter for the patient.

* * * * *